(12) United States Patent
Zhang et al.

(10) Patent No.: US 7,311,914 B2
(45) Date of Patent: Dec. 25, 2007

(54) MAGE-A4 ANTIGENIC PEPTIDES AND USES THEREOF

(75) Inventors: Yi Zhang, Brussels (BE); Vincent Stroobant, Brussels (BE); Vincenzo Russo, Milan (IT); Thierry Boon-Falleur, Brussels (BE); Pierre van der Bruggen, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 676 days.

(21) Appl. No.: 10/218,095

(22) Filed: Aug. 13, 2002

(65) Prior Publication Data

US 2004/0033541 A1    Feb. 19, 2004

(51) Int. Cl.
A61K 39/00 (2006.01)

(52) U.S. Cl. .................... 424/184.1; 530/300; 530/350; 424/185.1

(58) Field of Classification Search ................ 530/300, 530/350, 328; 514/2; 424/184.1, 185.1, 424/192.1
See application file for complete search history.

(56) References Cited

U.S. PATENT DOCUMENTS

| | | | |
|---|---|---|---|
| 5,342,774 A | 8/1994 | Boon et al. | |
| 5,405,940 A | 4/1995 | Boon et al. | |
| 5,487,974 A | 1/1996 | Boon-Falleur et al. | |
| 5,571,711 A | 11/1996 | van der Bruggen et al. | |
| 5,587,289 A | 12/1996 | Lurquin et al. | |
| 5,589,334 A | 12/1996 | Coulie et al. | |
| 5,610,013 A | 3/1997 | Van den Eynde et al. | |
| 5,620,886 A | 4/1997 | Brichard et al. | |
| 5,629,166 A | 5/1997 | van der Bruggen et al. | |

FOREIGN PATENT DOCUMENTS

| | | |
|---|---|---|
| WO | WO 92/20356 A1 | 11/1992 |
| WO | WO 96/10577 A1 | 11/1996 |

OTHER PUBLICATIONS

Roitt et al, Immunology, 4th ed, 1998, Mosby, New York, pp. 1.8, 7.10.*
Bowie et al (Science, 1990, 257:1306-1310).*
Long et al, Biochemical and biophysical research communications, Nov. 2, 1999, 264(3): p. 902-8.*
Ye et al, J med chem. 1995, 38: 4270-4275.*
Burgess et al, J of Cell Bio. 111:2129-2138, 1990.*
Lazar et al, Molecular and Cellular Biology, 1988, 8:1247-1252.*
Smith RT, 1994, Clin Immunol, 41(4): 841-849.*
Boon (Adv Can Res, 1992, 58:177-210).*
Ezzell (J. NIH Res, 1995, 7:46-49).*
Spitler (Cancer Biotherapy, 1995, 10:1-3).*
Kirkin et al, 1998, APMIS, 106 : 665-679.*
White et al, 2001, Ann Rev Med, 52: 125-145.*
Bergmann et al, 1994 (J Virol, 68(8): 5306-5310).*
Eisenlohr et al, 1992 (J Exp Med, 175:481-487).*
Shastri et al, 1995 (J Immunol, 155: 4339-4346).*
Guo et al, 1992 (Nature, 360: 364-366).*
Barinaga, "Getting Some 'Backbone': How MHC Binds Peptides," *Science* 1992, 257: 880-881.
Chaux et al., "Identification of MAGE-3 Epitopes Presented by HLA-DR Molecules to CD4$^+$T Lymphocytes," *J. Exp. Med.* 1999, 189, 5: 767-777.
Chen et al., "High frequency of expression of MAGE genes in human hepatocellular carcinoma," *Liver* 1999, 19: 110-1104.
Chomez et al., "Overview of the MAGE Gene Family with the Identification of All Human Mebers of the Family," *Cancer Research* 2001, 61: 5544-5551.
De Plaen et al., "Structure, chromosomal localization, and expression of 12 genes of the MAGE family," *Immunogenetics* 1994, 40: 360-369.
De Plaen et al., "Alternative Promoters of Gene MAGE4a," *Genomics* 1997, 40: 305-313.
Dalerba et al., "MAGE, BAGE and GAGE Gene Expression in Human Rhabdomyosarcomas," *Int. J. Cancer* 2001, 93: 85-90.
Duffour et al., "A MAGE-A4 peptide presented by HLA-A2 is recognized by cytolytic T lymphocytes," *Eur. J. Immunol.* 1999, 29: 3329-3337.
Espevik et al., "A highly sensitive cell line, WEHI 164 clone 13, for measuring cytotoxic factor/tumor necrosis factor from human monocytes," *Journal of Immunological Methods* 1986, 95: 99-105.
Falk et al., "Peptide motifs of HLA-B35 and -B37 molecules," *Immunogenetics* 1993, 38: 161-162.
Fremont et al., "Crystal Structures of Two Viral Peptides in Complex with Murine MHC Class I H-2K$^b$," *Science* 1992, 257: 919-927.
Haas Jr. et al., "Distribution of Human Leukocyte Antigen-ABC and -D/DR Antigens in the Unfixed Human Testis," *American Journal of Reproductive Immunology and Microbiology* 1988, 18: 47-51.
Hansen et al., "Re-examination and further development of a precise and rapid dye method for measuring cell growth/cell kill," *Journal of Immunological Methods* 1989, 119: 203-210.
Hunt et al., "Characterization of Peptides Bound to the Class I MHC Molecule HLA-A2.1 by Mass Spectrometry," *Science* 1992, 255: 1261-1263.
Jäger et al., "Clinical cancer vaccine trials," *Curr. Opin. Immunol.* 2002, 14: 178-182.
Latron et al., "A Critical Role for Conserved Residues in the Cleft of HLA-A2 in Presentation of a Nonapeptide to T Cells," *Science* 1992, 257: 964-967.
Lonchay et al., "Correlation between tumor regression and T cell responses in melanoma patients vaccinated with a MAGE antigen," *Proc. Natl. Acad. Sci. USA* 2004, 101 suppl. 2: 14631-14638.

(Continued)

*Primary Examiner*—Larry R. Helms
*Assistant Examiner*—Minh-Tam Davis
(74) *Attorney, Agent, or Firm*—Wolf, Greenfield & Sacks, P.C.

(57) ABSTRACT

The invention provides antigenic peptides derived from MAGE polypeptides and presented by HLA-B37 molecules. Methods for diagnosis and treatment which involve the polypeptides also are provided.

11 Claims, 6 Drawing Sheets

OTHER PUBLICATIONS

Lucas et al., "Identification of a New MAGE Gene with Tumor-specific Expression by Representational Difference Analysis," *Cancer Research* 1998, 58: 743-752.

Luiten et al., "A MAGE-A1 peptide is recognized on HLA-B7 human tumors by cytolytic T lymphocytes," *Tissue Antigens* 2000, 55: 149-152.

Lurquin et al., "Two Members of the Human MAGEB Gene Family Located in Xp21.3 Are Expressed in Tumors of Various Histological Origins," *Genomics* 1997, 46: 397-408.

Lurquin et al., "Contrasting frequencies of antitumor and anti-vaccine T cells in metastases of a melonoma patient vaccinated with a MAGE tumor antigen," *The Journal of Experimental Medicine* 2005, 201, 2: 249-257.

Male et al., *Advanced Immunology* (J.P. Lipincott Company, 1987), chapters 6-10.

Matsumura et al., "Emerging Principles for the Recongnition of Peptide Antigens by MHC Class I Molecules," *Science* 1992, 257: 927-934.

Marchand et al., "Biological and clinical developments in melanoma vaccines," *Exp. Opin. Biol. Ther.* 2001, 1,3: 497-510.

Marchand et al., "Tumor Regressions Observed in Patients with Metastatic Melanoma Treated with an Antigenic Peptide Encoded by Gene MAGE-3 and Presented by HLA-A1," *Int. J. Cancer* 1999, 80: 219-230.

Mavilio et al., "Peripheral Blood Lymphocytes as Target Cells of Retroviral Vector-Mediated Gene Transfer," *Blood* 1994: 83, 7: 1988-1997.

Rammensee et al., "MHC ligands and peptide motifs: first listing," *Immunogenetics* 1995, 41: 178-228.

Schultz et al., "A MAGE-3 peptide recognized on HLA-B35 and HLA-A1 by cytolytic T lymphocytes," *Tissue Antigens* 2001, 57: 103-109.

Thurner et al., "Vaccination with Mage-3A1 Peptide-pulsed Mature, Monocyte-derived Dendritic Cells Expands Specific Cytotoxic T Cells and Induces Regression of Some Metastases in Advanced Stage IV Melanoma," *J. Exp. Med.* 1999, 190, 11: 1669-1678.

Traversari et al., "A Nonapeptide Encoded by Human Gene MAGE-1 Is Recognized on HLA-A1 by Cytolytic T Lymphocytes Directed against Tumor Antigen MZ2-E," *J. Exp. Med.* 1992, 176: 1453-1457.

Traversari et al., "Transfection and expression of a gene coding for a human melanoma antigen recognized by autologous cytolytic T lymphocytes," *Immunogenetics* 1992, 35: 145-152.

Van Der Bruggen et al., "Tumor-specific shared antigenic peptides recognized by human T cells," *Immunological Reviews* 2002, 188: 51-64.

Van Der Bruggen et al., "Autologous cytolytic T lymphocytes recognize a MAGE-1 nonapeptide on melanomas expressing HLA-Cw* 1601*," *Eur. J. Immunol.* 1994, 24: 2134-2140.

Van Der Bruggen et al., "A Gene Encoding an Antigen Recognized by Cytolytic T Lymphocytes on a Human Melanoma," *Science* 1991, 254: 1643-1647.

Van Snick et al., "Interleukin-HP1, a T Cell-Derived Hybridoma Growth Factor that Supports the In Vitro Growth of Murine Plasmacytomas," *J. Exp. Med.* 1987, 165: 641-649.

\* cited by examiner

MAGE-A4 ANTIGENIC PEPTIDES AND USES THEREOF

FIELD OF THE INVENTION

This invention relates to polypeptides and encoded nucleic acid molecules which are expressed preferentially in tumors, including melanomas, bladder carcinomas, renal carcinomas, lung carcinomas, esophageal carcinomas, etc. The nucleic acid molecules and encoded polypeptides are useful in, inter alia, diagnostic and therapeutic contexts.

BACKGROUND OF THE INVENTION

The phenotypic changes which distinguish a tumor cell from its normal counterpart are often the result of one or more changes to the genome of the cell. The genes which are expressed in tumor cells, but not in normal counterparts, can be termed "tumor associated" genes. These tumor associated genes are markers for the tumor phenotype. The expression of tumor associated genes can also be an essential event in the process of tumorigenesis.

Typically, the host recognizes as foreign the tumor associated genes which are not expressed in normal non-tumorigenic cells. Thus, the expression of tumor associated genes can provoke an immune response against the tumor cells by the host. Tumor associated genes can also be expressed in normal cells within certain tissues without provoking an immune response. In such tissues, expression of the gene and/or presentation of an ordinarily immunologically recognizable fragment of the protein product on the cell surface may not provoke an immune response because the immune system does not "see" the cells inside these immunologically privileged tissues. Examples of immunologically privileged tissues include brain and testis.

The discovery of tumor associated expression of a gene provides a means of identifying a cell as a tumor cell. Diagnostic compounds can be based on the tumor associated gene, and used to determine the presence and location of tumor cells. Further, when the tumor associated gene contributes to an aspect of the tumor phenotype (e.g., unregulated growth or metastasis), the tumor associated gene can be used to provide therapeutics such as antisense nucleic acids which can reduce or substantially eliminate expression of that gene, thereby reducing or substantially eliminating the phenotypic aspect which depends on the expression of the particular tumor associated gene.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, *Science* 257: 880, 1992; Fremont et al., *Science* 257: 919, 1992; Matsumura et al., *Science* 257: 927, 1992; Latron et al., *Science* 257: 964, 1992.

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *J. Exp. Med.* 176:1453–1457, 1992; van der Bruggen et al., *Science* 254: 1643,1991; De Plaen et al., *Immunogenetics* 40:360–369, 1994 and U.S. Pat. No. 5,342,774 for further information on this family of genes.

In U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,629,166, incorporated by reference, the fact that the MAGE-1 expression product is processed to a second TRA is disclosed. This second TRA is presented by HLA-Cw16 molecules, also known as HLA-C*1601. The disclosure shows that a given TRAP can yield a plurality of TRAs.

In U.S. Pat. No. 5,487,974, incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. Pat. No. 5,620,886, incorporated herein by reference in its entirety, a second TRA, not derived from tyrosinase is taught to be presented by HLA-A2 molecules. The TRA is derived from a TRAP, but is coded for by a known MAGE gene. This disclosure shows that a particular HLA molecule may present TRAs derived from different sources.

Additional TRAPs are disclosed in U.S. Pat. Nos. 5,571, 711, 5,610,013, 5,587,289 and 5,589,334, as well as PCT publication WO96/10577. The TRAPs are processed to tumor rejection antigens, which are presented by a variety of HLA molecules.

There exist many patients who would benefit from therapy which includes additional antigenic peptides, either because the patient's tumor does not express previously known antigenic peptides, or because the patient does not express the appropriate HLA molecule. Accordingly, there is a need for the identification of additional tumor associated antigens which contain epitopes presented by MHC class I molecules and recognized by CD8[+] lymphocytes.

SUMMARY OF THE INVENTION

It now has been discovered that the human MAGE-A4 gene encodes a tumor rejection antigen presented by HLA-B37. Peptides derived from the MAGE-A4 polypeptide (SEQ ID NO:2), when presented by an antigen presenting cell having an HLA-B37 molecule, effectively induce the activation and proliferation of CD8+ cytotoxic T lymphocytes. Further, homologous peptides from other MAGE proteins are provided herein, and can be used in a similar manner as the disclosed MAGE-A4 peptides.

According to one aspect of the invention, an isolated MAGE-A4 HLA class I-binding peptide is provided. The peptide includes the amino acid sequence of SEQ ID NO:6, or a functional variant thereof which binds HLA class I molecules. The functional variant includes 1–5 amino acid additions to, substitutions of and/or deletions of the amino acid sequence of SEQ ID NO:6. In certain embodiments, the isolated MAGE-A4 HLA class I-binding peptide includes an amino acid sequence selected from the group consisting of SEQ ID NO:3, SEQ ID NO:4, SEQ ID NO:5, SEQ ID NO:6, SEQ ID NO:8, SEQ ID NO:9, fragments thereof, and functional variants thereof. In preferred embodiments, the isolated peptide consists of an amino acid sequence selected from the group consisting of SEQ ID NO:3, SEQ ID NO:4, SEQ ID NO:5, SEQ ID NO:6, SEQ ID NO:8, SEQ ID NO:9, fragments thereof, and functional variants thereof. The isolated MAGE-A4 HLA class I-binding peptide preferably is not the full length MAGE-A4 polypeptide sequence.

According to another aspect of the invention, an isolated MAGE-A4 HLA class I binding peptide is provided which includes a fragment of the amino acid sequence of SEQ ID NO:2 which binds HLA-B37, or a functional variant thereof. The functional variant includes 1–5 amino acid additions to, substitutions of and/or deletions of the amino acid sequence of SEQ ID NO:6. The functional variant binds HLA-B37. Preferred embodiments include SEQ ID NO:3, SEQ ID NO:4, SEQ ID NO:5, SEQ ID NO:6, SEQ ID NO:8, and SEQ ID NO:9.

In some embodiments, the foregoing isolated MAGE-A4 HLA class I-binding peptides are non-hydrolyzable. Preferably the non-hydrolyzable peptide is selected from the group consisting of peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

Also provided according to an aspect of the invention are compositions including the foregoing isolated MAGE-A4 HLA class I-binding peptides and one or more isolated HLA class I- or class II-binding peptides of non-MAGE-A4 tumor antigens. Preferably the MAGE-A4 HLA class I-binding peptides and the non-MAGE-A4 HLA binding peptides are combined as a polytope polypeptide.

According to another aspect of the invention, isolated nucleic acids encoding the foregoing peptides are provided. The nucleic acids do not encode full length MAGE polypeptides, e.g., MAGE-A4. In certain embodiments, the nucleic acids comprise a fragment of the nucleotide sequence of SEQ ID NO:1. Expression vectors are also provided according to the invention. The expression vectors include the isolated foregoing nucleic acids operably linked to a promoter. In certain embodiments, the expression vectors also include a nucleic acid which encodes an HLA-B37 molecule. In another aspect of the invention, host cells transfected or transformed with the foregoing nucleic acids or expression vectors are provided. In certain embodiments, the host cells also express an HLA-B37 molecule.

According to yet another aspect of the invention, methods for enriching selectively a population of T lymphocytes with T lymphocytes specific for a MAGE-A4 HLA-B37 binding peptide are provided. The methods include contacting a source of T lymphocytes which contains a population of T lymphocytes with an agent presenting a complex of the MAGE-A4 HLA-B37 binding peptide and an HLA molecule in an amount sufficient to selectively enrich the population of T lymphocytes with the T lymphocytes specific for a MAGE-A4 HLA-B37 binding peptide. In certain embodiments, the agent is an antigen presenting cell contacted with a MAGE-A4 protein or an HLA-B37 binding fragment thereof. In other embodiments, the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to still another aspect of the invention, methods for diagnosing a disorder characterized by expression of MAGE-A4 are provided. The methods include contacting a biological sample isolated from a subject with an agent that is specific for a MAGE-A4 HLA-B37 binding peptide, and determining the interaction between the agent and the MAGE-A4 HLA-B37 binding peptide as a determination of the disorder. Preferably the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

In another aspect of the invention, methods for diagnosing a disorder characterized by expression of a MAGE-A4 HLA-B37 binding peptide are provided. The methods include contacting a biological sample isolated from a subject with an agent that binds the complex and determining binding between the complex and the agent as a determination of the disorder. In certain embodiments, the MAGE-A4 HLA-B37 binding peptide is selected from the group consisting (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to still another aspect of the invention, methods for treating a subject having a disorder characterized by expression of MAGE-A4 are provided. The methods include administering to the subject an amount of a MAGE-A4 HLA-B37 binding peptide sufficient to ameliorate the disorder. In certain embodiments, the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to another aspect of the invention, methods for treating a subject having a disorder characterized by expression of MAGE-A4 are provided. The methods include administering to the subject an amount of a composition which included an isolated MAGE-A4 HLA-B37 binding peptide and an isolated HLA class I- or class II-binding peptide of a non-MAGE-A4 tumor antigen sufficient to ameliorate the disorder.

According to yet another aspect of the invention, methods for treating a subject having a disorder characterized by expression of MAGE-A4 are provided. The methods include administering to the subject an amount of an agent which enriches selectively in the subject the presence of complexes of an HLA molecule and a MAGE-A4 HLA-B37 binding peptide, sufficient to ameliorate the disorder. In certain embodiments, the agent includes a MAGE-A4 HLA-B37 binding peptide. In preferred embodiments, the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to a further aspect of the invention, methods for treating a subject having a disorder characterized by expression of MAGE-A4 are provided. The methods include administering to the subject an amount of autologous T lymphocytes sufficient to ameliorate the disorder, wherein the T lymphocytes are specific for complexes of an HLA molecule and a MAGE-A4 HLA-B37 binding peptide. In some embodiments, the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

Also provided according to another aspect of the invention are methods for identifying functional variants of a MAGE-A4 HLA-B37 binding peptide. The methods include selecting a MAGE-A4 HLA-B37 binding peptide, an HLA binding molecule which binds the MAGE-A4 HLA-B37 binding peptide, and a T cell which is stimulated by the MAGE-A4 HLA-B37 binding peptide presented by the HLA binding molecule; mutating a first amino acid residue of the MAGE-A4 HLA-B37 binding peptide to prepare a variant peptide; and determining the binding of the variant peptide to HLA binding molecule and the stimulation of the T cell, wherein binding of the variant peptide to the HLA binding molecule and stimulation of the T cell by the variant peptide presented by the HLA binding molecule indicates that the variant peptide is a functional variant. In certain embodiments, the MAGE-A4 HLA-B37 binding peptide is selected from the group consisting of (i) peptides which consist of a fragment of the amino acid sequence of SEQ ID NO:2, and (ii) peptides which comprise the amino acid sequence of SEQ ID NO:6. In other embodiments, the methods include the step of comparing the stimulation of the T cell by the MAGE-A4 HLA-B37 binding peptide and the stimulation of the T cell by the functional variant as a determination of the effectiveness of the stimulation of the T cell by the functional variant. Also provided are isolated functional variants of a MAGE-A4 HLA-B37 binding peptide identified by the methods.

According to another aspect of the invention, isolated polypeptides are provided which bind selectively the foregoing MAGE-A4 HLA-B37 binding peptides or a complex of an HLA molecule and a MAGE-A4 HLA-B37 binding peptide, provided that the isolated polypeptides are not HLA molecules. In some embodiments, the isolated polypeptides are antibodies, preferably monoclonal antibodies. In other embodiments the isolated polypeptides are antibody fragments selected from the group consisting of Fab fragments, F(ab)$_2$ fragments, Fv fragments or fragments including a CDR3 region selective for a MAGE-A4 HLA-B37 binding peptide.

According to still another aspect of the invention, isolated T lymphocytes which selectively bind a complex of an HLA molecule and a MAGE-A4 HLA-B37 binding peptide are provided. In some embodiments, the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to a further aspect of the invention, isolated antigen presenting cells which include a complex of an HLA molecule and a MAGE-A4 HLA-B37 binding peptide are provided. In certain embodiments, the MAGE-A4 HLA-B37 binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to yet another aspect of the invention, methods for identifying a candidate mimetic of a MAGE-A4 HLA-B37 binding peptide are provided. The methods include providing a HLA molecule which binds the MAGE-A4 HLA-B37 binding peptide, contacting the HLA molecule with a test molecule, and determining the binding of the test molecule to the HLA molecule, wherein a test molecule which binds to the HLA molecule is a candidate mimetic of the MAGE-A4 HLA-B37 binding peptide. In some embodiments, the methods include forming a complex of the HLA molecule and the candidate mimetic, contacting the complex with a T cell which binds to a complex of an HLA molecule and the MAGE-A4 HLA-B37 binding peptide, and assaying activation of the T cell. In certain of these methods, activation of the T cell is indicated by a property selected from the group consisting of proliferation of the T cell, interferon-y production by the T cell, tumor necrosis factor production by the T cell, and cytolysis of a target cell by the T cell.

According to a further aspect of the invention vaccine compositions are provided. The vaccine compositions can include the foregoing MAGE-A4 HLA-B37 binding peptides, the foregoing T lymphocytes, the foregoing antigen presenting cells, and/or the foregoing isolated nucleic acid molecules. In certain embodiments, the foregoing vaccine compositions include an adjuvant and/or a pharmaceutically acceptable carrier.

In another aspect of the invention, protein microarrays that include one or more isolated MAGE-A4 HLA-B37 binding peptides, or functional variants thereof that bind HLA class I molecules, are provided. The functional variants include 1–5 amino acid additions, substitutions or deletions. In some embodiments the isolated MAGE-A4 HLA-B37 binding peptides include the amino acid sequence of SEQ ID NO:6. In other embodiments the isolated MAGE-A4 HLA-B37 binding peptides include an amino acid sequence selected from the group consisting of SEQ ID NO:3, SEQ ID NO:4, SEQ ID NO:5, SEQ ID NO:6, SEQ ID NO:8, SEQ ID NO:9, and functional variants thereof. The use of such microarrays in diagnostic applications, particularly for diagnosing cancer, also is provided. The diagnostic methods include contacting the protein microarray with a biological sample isolated from a subject suspected of having the disorder, and determining the binding of a constituent of the biological sample to the isolated MAGE-A4 HLA-B37 binding peptide. In certain embodiments the constituent of the biological sample is selected from the group consisting of an antibody, a T lymphocyte, and a HLA molecule. Preferably the disorder is cancer.

The invention also provides pharmaceutical preparations containing any one or more of the compositions described herein. Such pharmaceutical preparations can include pharmaceutically acceptable diluent carriers or excipients. The use of such compositions in the preparation of medicaments, particularly medicaments for the treatment of cancer also is provided.

In the foregoing methods and compositions, the MAGE-A4 HLA-B37 binding peptide preferably comprises an amino acid sequence selected from the group consisting of SEQ ID NO:3, SEQ ID NO:4, SEQ ID NO:5, SEQ ID NO:6, SEQ ID NO:8, SEQ ID NO:9. In certain preferred embodiments, the MAGE-A4 HLA-B37 binding peptide binds HLA-B*3701. In additional embodiments of the methods and compositions described herein, HLA-B37 binding peptides from other MAGE proteins include amino acid sequences selected from the group consisting of SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63, such as fragments of MAGE-A1, MAGE-A2, MAGE-A3, MAGE-A6, MAGE-A8, MAGE-A10, MAGE-A11, and/or MAGE-A12, and functional variants thereof.

Disorders as used herein include cancers, such as bladder carcinomas, melanomas, esophageal carcinomas, lung carcinomas, head and neck carcinomas, breast carcinomas, colorectal carcinomas, hepatocellular carcinomas, leukemias, myclomas, rhabdomyosarcomas, sarcomas and renal carcinomas.

These and other objects of the invention will be described in further detail in connection with the detailed description of the invention.

BRIEF DESCRIPTION OF THE FIGURES

FIG. 3 depicts peptide titration experiments.

DETAILED DESCRIPTION OF THE INVENTION

Figure 1:
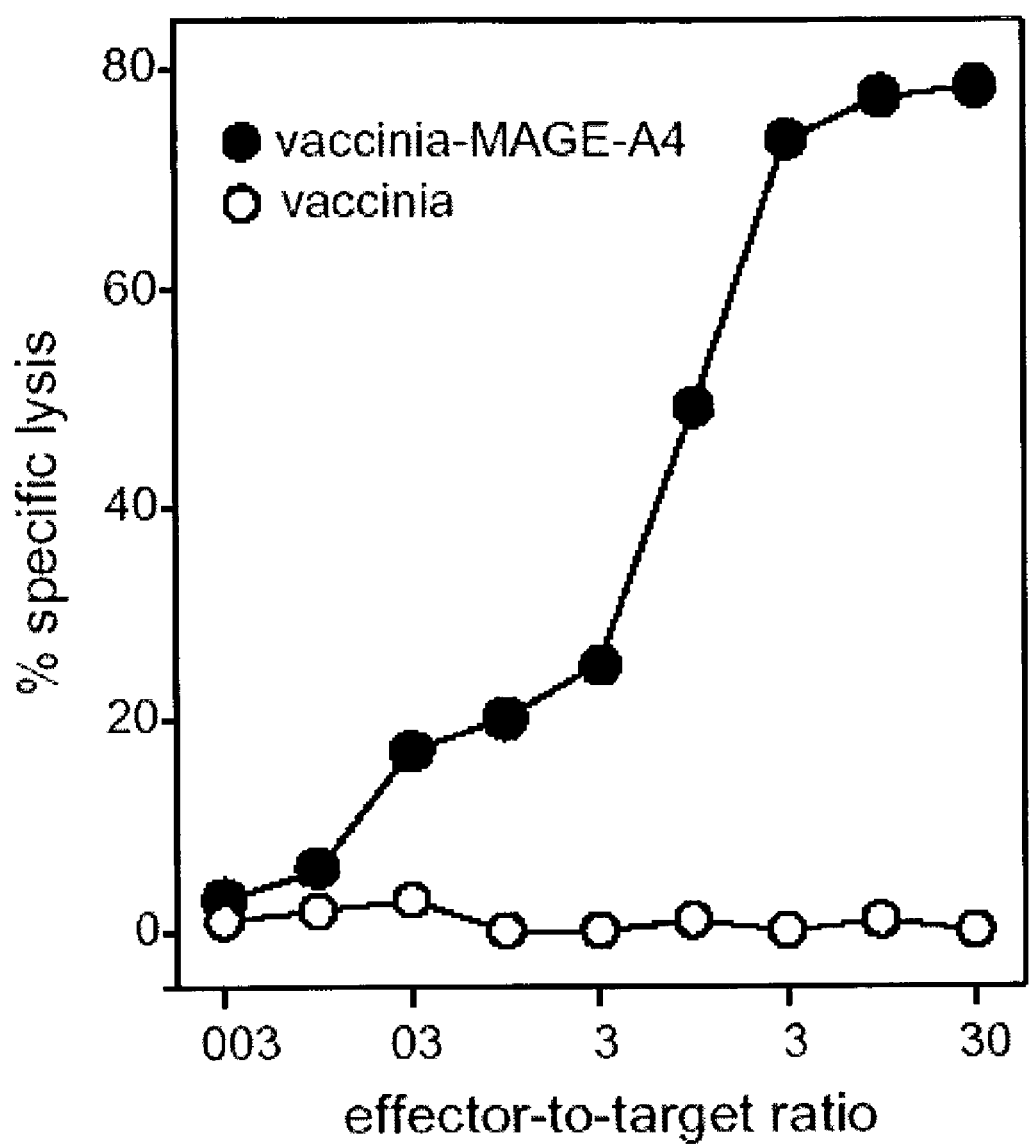
FIG. 1 shows lysis by CTL F2 of autologous EBV-B cells infected with vaccinia-MAGE-A4. EBV-B cells from donor LB2257 were infected for 2 h with the vaccinia vectors at a multiplicity of infection of 20, $^{51}$Cr-labeled for 1 h, and incubated with autologous CTL F2 at the indicated effector-to-target ratios. Chromium release was measured after 4 h.

"Cancer-germline" genes such as those of the MAGE family are expressed in many tumors and in male germline cells, but are silent in normal tissues. They encode shared tumor-specific antigens, which have been used in therapeutic vaccination trials of cancer patients. MAGE-A4 is expressed in more than 50% of carcinomas of esophagus, head and neck, lung, and bladder. New MAGE-A4 encoded peptides have been identified, which are recognized by a cytolytic T lymphocyte (CTL) clone on HLA-B*3701. The sequence of the shortest peptide efficiently recognized by HLA-B37 is SESLKMIF (SEQ ID NO:6). It corresponds to the MAGE-A4$_{156-163}$ protein sequence (amino acids 156–163 of the MAGE-A4 protein sequence, SEQ ID NO:2). When tumor cells expressing MAGE-A4 were transfected with HLA-B*3701, they were recognized by the CTL clone, demonstrating that the peptide is processed and presented by tumor cells and could therefore serve as target for therapeutic anti-tumoral vaccination.

MAGE-A4 belongs to the MAGE gene family which comprises 24 related functional genes divided into three clusters, named MAGE-A, B, and C (1–4). These genes are expressed in many human tumors of different histological types, but are silent in normal cells with the exception of testis. Some of them, including MAGE-A4, are also expressed in placenta (1). Male germline cells and placenta do not express MHC class I molecules and are therefore incapable of presenting antigens to CTL (5, 6). MAGE-encoded antigens are thus tumor-specific and of particular interest for cancer immunotherapy because they are shared by many tumors. Clinical trials involving defined tumor-specific shared antigens have been and are being performed in melanoma patients, and tumor regressions have been observed in a minority of patients (7–10).

There are two known alleles of gene MAGE-A4, MAGE-A4a and MAGE-A4b. They code for proteins that differ by a single amino acid (11). The gene contains eight alternative first exons that are spliced to unique second and third exons. The entire open reading frame is located in the third exon. The role of the different first exons, each with their own promoter, is unknown. The coding sequence of MAGE-A4a (SEQ ID NO:1; the encoded polypeptide is SEQ ID NO:2), referred to herein as MAGE-A4 was used in this work. MAGE-A4 is expressed in a significant proportion of tumors (see Table 1).

TABLE 1

Expression of gene MAGE-A4 by tumoral tissues[a]

| Histological type | Percentage | (n[b]) |
|---|---|---|
| Bladder carcinoma: superficial (<T2) | 23 | (70) |
| Bladder carcinoma: infiltrating (≧T2) | 45 | (53) |

TABLE 1-continued

Expression of gene MAGE-A4 by tumoral tissues[a]

| Histological type | Percentage | (n[b]) |
|---|---|---|
| Breast carcinoma | 6 | (135) |
| Colorectal carcinoma | 11 | (46) |
| Esophageal squamous-cell carcinoma | 74 | (19) |
| Head & neck squamous-cell carcinoma | 53 | (85) |
| Hepatocellular carcinoma | 16 | (50) |
| Leukemia | 1 | (112) |
| Lung carcinoma: squamous-cell carcinoma | 59 | (93) |
| Lung carcinoma: adenocarcinoma | 35 | (43) |
| Melanoma: primary lesions | 18 | (83) |
| Melanoma: metastases | 28 | (243) |
| Myeloma: stages I–II | 0 | (11) |
| Myeloma: stage III | 22 | (27) |
| Pediatric rhabdomyosarcoma | 22 | (31) |
| Prostate carcinoma | 0 | (22) |
| Renal cell carcinoma | 2 | (44) |
| Sarcoma | 33 | (15) |

[a]Expression was measured by RT-PCR on total RNA of surgical samples using primer specific for MAGE-A4. All the results have been obtained by Francis Brasseur at the Brussels Branch of the Ludwig Institute for Cancer Research (25), except for hepatocellular carcinoma (26) and pediatric rhabdomyosarcoma (27).
[b]n = number of tumors tested.

Thus, in accordance with the findings described herein, Applicants have identified a series of peptides from MAGE-A4 that are HLA-B37 binding peptides. These include FPVIFGKASESLKMIF (SEQ ID NO:3); SESLKMIFGID-VKEVD (SEQ ID NO:4); SESLKMIFGI (SEQ ID NO:5); and SESLKMIF (SEQ ID NO:6); as well several functional variant peptides with amino acids added at the carboxyl termins of the SESLKMIF peptide (SEQ ID NO:6): SESLK-MIFI (SEQ ID NO:8); and SESLKMIFL (SEQ ID NO:9).

Homologous peptides from other members of the MAGE protein family also are useful in stimulating T cells via HLA-B37 binding and presentation as described herein more particularly for MAGE-A4 peptides, and include the following MAGE peptides presented in Table 2. The preferred homologous peptides share two potential anchor residues for HLA-B37 (E/D in position 2 and F in the C-terminal position), i.e., those from MAGE-A1, MAGE-A2, MAGE-A6, MAGE-A8, MAGE-A10 and MAGE-A12.

defined antigenic peptides. A large set of peptide/HLA combinations will alleviate HLA restriction and widen the set of eligible patients. It will also facilitate the design of concurrent immunizations against several antigens. Such immunizations could increase the primary anti-tumor efficacy of the vaccine and also decrease the risk of tumor escape by loss of antigen expression.

To isolate the first MAGE-A4-specific CTL, CD8[+] T cells from non-cancerous blood donors were stimulated with autologous dendritic cells infected with an adenovirus carrying the coding sequence of MAGE-A4. Here, a slightly different strategy was used: the dendritic stimulator cells were infected with an avian poxvirus, ALVAC, carrying the coding sequence of MAGE-A4. Using this strategy, a new MAGE-A4 antigen was identified.

The invention provides isolated MAGE-A4 peptides, some of which are presented by HLA-B37 molecules, which peptides stimulate the activation of CD8[+] T lymphocytes. The peptides can also be used to stimulate proliferation of CD8[+] T lymphocytes. Such peptides are referred to herein as "MAGE-A4 immunogenic polypeptides," "MAGE-A4 HLA-B37 binding peptides," "MAGE-A4 HLA-B*3701 binding peptides," and "MAGE-A4 HLA peptides," and the like. Hence, one aspect of the invention is an isolated peptide which includes the amino acid sequence of SEQ ID NO:6. The invention also provides isolated peptides from related MAGE proteins that bind to HLA-B37, such as those presented in Table 2, and preferably the peptides derived from MAGE-A1, MAGE-A2, MAGE-A6, MAGE-A8, MAGE-A10 and MAGE-A12. Collectively, the HLA-B37 binding peptides derived from MAGE proteins are known as "MAGE HLA-B37 binding peptides."

The examples below show the isolation of peptides which are MAGE-A4 HLA binding peptides. These exemplary peptides are processed translation products of the MAGE-A4 nucleic acid coding sequence (SEQ ID NO:1), i.e., fragments of the MAGE-A4 protein (the amino acid sequence of which is provided as SEQ ID NO:2). As such, it will be appreciated by one of ordinary skill in the art that the translation products from which a MAGE-A4 immunogenic polypeptide is processed to a final form for presentation may be of any length or sequence so long as they

TABLE 2

HLA-B37 peptides from MAGE-family proteins

| Protein | Octamer peptide (MAGE amino acids) | SEQ ID NO | Decamer peptide (MAGE amino acids) | SEQ ID NO |
|---|---|---|---|---|
| MAGE-A4 | SESLKMIF (156–163) | 6 | SESLKMIFGI (156–165) | 5 |
| MAGE-A1 | SESLQLVF (148–155) | 48 | SESLQLVFGI (148–157) | 49 |
| MAGE-A2 | SEYLQLVF (155–162) | 50 | SEYLQLVFGI (155–164) | 51 |
| MAGE-A3 | SSSLQLVF (155–162) | 52 | SSSLQLVFGI (155–164) | 53 |
| MAGE-A6 | SDSLQLVF (155–162) | 54 | SDSLQLVFGI (155–164) | 55 |
| MAGE-A8 | SECMQVIF (158–165) | 56 | SECMQVIFGI (158–167) | 57 |
| MAGE-A10 | SECMLLVF (180–187) | 58 | SECMLLVFGI (180–189) | 59 |
| MAGE-A11 | SVCMQLLF (158–165) | 60 | SVCMQLLFGI (158–167) | 61 |
| MAGE-A12 | SEYLQLVF (155–162) | 62 | SEYLQLVFGI (155–164) | 63 |

MAGE-A4 peptide GVYDGREHTV (MAGE-A4$_{230-239}$; SEQ ID NO:10) was reported previously to be recognized by cytolytic T lymphocytes (CTL) on HLA-A2 (12). Thus, only one antigenic peptide has been hitherto identified in the MAGE-A4 protein. The identification of a large number of antigenic peptides presented by HLA class I and class II is likely to be important for the future of clinical trials with encompass an HLA binding peptide. In certain instances, the HLA binding peptides include a MAGE-A4 HLA binding peptide having an amino acid sequence as set forth in SEQ ID NOs:3, 4, 5, 6, 8 or 9. As demonstrated in the examples below, peptides or proteins as small as 8 amino acids are appropriately processed, presented by HLA class I molecules and effective in stimulating CD8[+] T lymphocytes.

The peptide of SEQ ID NOs: 3, 4, 5, 6, 8 or 9 may have one, two, three, four, five, six, seven, eight, nine, ten, or more amino acids added to either or both ends. The added amino acids can correspond to the MAGE-A4 polypeptide (SEQ ID NO:2), or can be unrelated. When a fragment of the MAGE-A4 polypeptide is used in the methods and compositions described herein, it will include SEQ ID NO:6 and it preferably will be less than about 90% of the whole protein sequence, more preferably less than about 75% of the protein sequence, yet more preferably less than about 50% of the protein sequence, still more preferably less than about 25% of the protein sequence, and most preferably less than about 10% of the protein sequence. As is well known in the art, the antigenic portion of such a peptide is cleaved out under physiological conditions for presentation by HLA class I molecules.

Additional HLA binding peptides derived from the MAGE-A4 polypeptide may provoke an immune response when presented by HLA B37 molecules. The invention embraces all such immunogenic fragments of the MAGE-A4 polypeptide.

As noted above, the invention embraces functional variants of the MAGE-A4 HLA binding peptides. As used herein, a "functional variant" or "variant" of a MAGE-A4 HLA binding peptide is a molecule which contains one or more modifications to the primary amino acid sequence of the MAGE-A4 HLA binding peptide and retains the HLA class I binding properties disclosed herein, as well as the ability to stimulate proliferation and/or activation of $CD8^+$ T lymphocytes. Modifications which create a MAGE-A4 immunogenic polypeptide functional variant can be made for example 1) to enhance a property of a MAGE-A4 HLA binding peptide, such as peptide stability in an expression system or the stability of protein-protein binding such as HLA-peptide binding; 2) to provide a novel activity or property to a MAGE-A4 immunogenic polypeptide, such as addition of an antigenic epitope or addition of a detectable moiety; or 3) to provide a different amino acid sequence that produces the same or similar T cell stimulatory properties. Modifications to a MAGE-A4 HLA binding peptide can be made to a nucleic acid which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. In preferred embodiments, such variant peptides will have 1, 2, 3, 4, or 5 amino acid additions, substitutions and/or deletions. Modifications also embrace fusion proteins comprising all or part of the MAGE-A4 immunogenic polypeptide amino acid sequence.

The amino acid sequence of MAGE-A4 immunogenic polypeptides may be of natural or non-natural origin, that is, they may comprise a natural MAGE-A4 immunogenic polypeptide molecule or may comprise a modified sequence as long as the amino acid sequence retains the ability to stimulate cytolytic T cells when presented and retains the property of binding to an HLA class I molecule such as an HLA-B37 molecule. For example, MAGE-A4 immunogenic polypeptides in this context may be fusion proteins of a MAGE-A4 HLA binding peptide and related or unrelated amino acid sequences, synthetic peptides of amino acid sequences shown in SEQ ID NOs:3, 4, 5, 6, 8 and 9, labeled peptides, peptides isolated from patients with a MAGE-A4 expressing cancer, peptides isolated from cultured cells which express MAGE-A4, peptides coupled to nonpeptide molecules (for example in certain drug delivery systems) and other molecules which include the amino acid sequence of SEQ ID NO:6.

Preferably, MAGE-A4 HLA binding peptides are non-hydrolyzable. To provide such peptides, one may select MAGE-A4 HLA binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing $CD8^+$ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a MAGE-A4 immunogenic polypeptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi [$CH_2NH$]-reduced amide peptide bonds, -psi[$COCH_2$]-ketomethylene peptide bonds, -psi[$CH(CN)NH$]-(cyanomethylene)amino peptide bonds, -psi[$CH_2CH(OH)$]-hydroxyethylene peptide bonds, -psi[$CH_2O$]-peptide bonds, and -psi[$CH_2S$]-thiomethylene peptide bonds.

Nonpeptide analogs of peptides, e.g., those which provide a stabilized structure or lessened biodegradation, are also contemplated. Peptide mimetic analogs can be prepared based on a selected MAGE-A4 HLA binding peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., Regul. Pept. 57:359–370 (1995). Peptide mimetics also can be selected from libraries of synthetic compounds (e.g. combinatorial libraries of small organic molecules) or natural molecules according to the HLA binding properties and/or T cell stimulatory properties of such molecule. Assays for identification of mimetics of a MAGE-A4 immunogenic polypeptide from libraries such as binding assays are well known in the art. Peptide as used herein embraces all of the foregoing.

If a variant involves a change to an amino acid of a MAGE-A4 immunogenic polypeptide (e.g., SEQ ID NOs:3, 4, 5, 6, 8 or 9), functional variants of the MAGE-A4 immunogenic polypeptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the MAGE-A4 immunogenic polypeptides are provided in a published PCT application of Strominger and Wucherpfennig (US/96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Sequence motifs for MAGE-A4 HLA binding peptide functional variants can be developed by analysis of the binding domains or binding pockets of major histocompatibility complex HLA-B37 proteins and/or the T cell receptor ("TCR") contact points of the MAGE-A4 immunogenic polypeptides disclosed herein. By providing a detailed structural analysis of the residues involved in forming the HLA class I binding pockets, one of ordinary skill in the art is enabled to make predictions of sequence motifs for binding to any of the HLA class I proteins.

Using these sequence motifs as search, evaluation, or design criteria, one of ordinary skill in the art is enabled to identify classes of peptides (functional variants of the MAGE-A4 HLA binding peptides disclosed herein) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. Likewise, by keeping the residues which are likely to bind in the HLA class I and/or TCR binding pockets constant or permitting only specified substitutions, functional variants of the MAGE-A4 HLA binding peptides can be prepared which retain binding to HLA class I and T cell receptor.

Localization of one or more antigenic peptides in a protein sequence can be aided by HLA peptide binding predictions made according to established rules for binding potential (e.g., Parker et al, *J. Immunol.* 152:163, 1994; Rammensee et al., *Immunogenetics* 41:178–228, 1995). HLA binding predictions can conveniently be made using an algorithm available via the Internet on the National Institutes of Health World Wide Web site at URL http://bimas.dcrt.nih.gov.

Thus methods for identifying functional variants of a MAGE-A4 immunogenic polypeptide are provided. In general, the methods include selecting a MAGE-A4 HLA binding peptide, an HLA class I binding molecule which binds the MAGE-A4 HLA binding peptide, and a T cell which is stimulated by the MAGE-A4 HLA binding peptide presented by the HLA class I binding molecule. In preferred embodiments, the MAGE-A4 immunogenic polypeptide comprises the amino acid sequence of SEQ ID NO:6. More preferably, the peptide comprises or consists of the amino acid sequence of SEQ ID NO:3, SEQ ID NO:4, SEQ ID NO:5, SEQ ID NO:6, SEQ ID NO:8 or SEQ ID NO:9. A first amino acid residue of the MAGE-A4 HLA binding peptide is mutated to prepare a variant peptide. The amino acid residue can be mutated according to the principles of HLA and T cell receptor contact points set forth above. Any method for preparing variant peptides can be employed, such as synthesis of the variant peptide, recombinantly producing the variant peptide using a mutated nucleic acid molecule, and the like.

The binding of the variant peptide to HLA class I binding molecule and/or stimulation of the T cell are then determined according to standard procedures. For example, as exemplified below, the variant peptide can be contacted with an antigen presenting cell which contains the HLA class I molecule which binds the MAGE-A4 HLA binding peptide to form a complex of the variant peptide and antigen presenting cell. This complex can then be contacted with a T cell which recognizes the MAGE-A4 HLA binding peptide presented by the HLA class I binding molecule. T cells can be obtained from a patient having a condition characterized by expression of MAGE-A4. Recognition of variant peptides by the T cells can be determined by measuring an indicator of T cell stimulation such as TNF or IFNγ production.

Binding of the variant peptide to the HLA class I binding molecule and/or stimulation of the T cell by the variant peptide presented by the HLA class I binding molecule indicates that the variant peptide is a functional variant. The methods also can include the step of comparing the stimulation of the T cell by the MAGE-A4 HLA binding peptide and the stimulation of the T cell by the functional variant as a determination of the effectiveness of the stimulation of the T cell by the functional variant. By comparing the functional variant with the MAGE-A4 HLA binding peptide, peptides with increased T cell stimulatory properties can be prepared.

Variants of the MAGE-A4 HLA binding peptides prepared by any of the foregoing methods can be sequenced, if necessary, to determine the amino acid sequence and thus deduce the nucleotide sequence which encodes such variants.

Thus those nucleic acid sequences which code for a MAGE-A4 immunogenic polypeptide or variant thereof, including allelic variants, are also a part of the invention. In screening for nucleic acids which encode a MAGE-A4 immunogenic polypeptide, a nucleic acid hybridization such as a Southern blot or a Northern blot may be performed under stringent conditions, together with a $^{32}P$ probe. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary stringent conditions include hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15 M Sodium Chloride/0.015M Sodium Citrate, pH 7; SDS is Sodium Dodecyl Sulphate; and EDTA is ethylene diaminetetraacetic acid. After hybridization, the membrane upon which the DNA is transferred can be washed, for example, at 2×SSC at room temperature and then at 0.1–0.5×SSC/0.1×SDS at temperatures up to 68° C. After washing the membrane to which DNA encoding a MAGE-A4 immunogenic polypeptide was finally transferred, the membrane can be placed against X-ray film or phosphorimager detection systems to detect the radioactive signal.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the MAGE-A4 immunogenic polypeptides of the invention. The skilled artisan also is familiar with the methodology for screening cells and libraries for expression of such molecules which then are routinely isolated, followed by isolation of the pertinent nucleic acid molecule and sequencing.

The invention also includes the use of nucleic acid sequences which include alternative codons that encode the same amino acid residues of the MAGE-A4 immunogenic polypeptides. For example, as disclosed herein, the peptide SESLKMIFGIDVKEVD (SEQ ID NO:4) is a MAGE-A4 HLA binding peptide. The leucine residues can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the MAGE-A4 HLA binding peptide of SEQ ID NO:4 include: GUA, GUC, GUG and GUU (valine codons); GGU, GGA, GGG, GGC (glycine codons). Other amino acid residues may be encoded similarly by multiple nucleotide sequences. Thus, the invention embraces degenerate nucleic acids that differ from the native MAGE-A4 immunogenic polypeptide encoding nucleic acids in codon sequence due to the degeneracy of the genetic code.

Preferred nucleic acids encoding MAGE-A4 polypeptides are those which preferentially express MAGE-A4 immunogenic polypeptides, such as the HLA binding peptide described herein. The MAGE-A4 nucleic acids of the invention do not encode the entire MAGE-A4 polypeptide (i.e., at most, a fragment of MAGE-A4 polypeptide comprising SEQ ID NO:6 is encoded) but do include nucleotide sequences encoding the MAGE-A4 HLA binding peptide.

The invention also provides modified nucleic acid molecules which include additions, substitutions and/or deletions of one or more nucleotides, preferably 1–15 nucleotides that encode 1–5 amino acids within the portion of the polypeptide that binds HLA-B37. In preferred embodiments, these modified nucleic acid molecules and/or the polypeptides they encode retain at least one activity or function of the unmodified nucleic acid molecule and/or the polypeptides, such as antigenicity, enzymatic activity, receptor binding, formation of complexes by binding of peptides by MHC class I and class II molecules, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared (e.g., preferably not those amino acids which are contact points for HLA binding). Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. In addition, as it has been found that human HLA-B*3701 molecules present a MAGE-A4 HLA class I binding peptide, the expression vector may also include a nucleic acid sequence coding for an HLA-B*3701 molecule. (For other class I or class II binding peptides, different HLA molecules can be used.) In a situation where the vector contains both coding sequences, it can be used to transfect a cell which does not normally express either one. The MAGE-A4 HLA class I binding peptide coding sequence may be used alone, when, e.g. the host cell already expresses an HLA-B*3701 molecule. Of course, there is no limit on the particular host cell which can be used as the vectors which contain the two coding sequences may be used in host cells which do not express HLA-B*3701 molecules if desired, and the nucleic acid coding for the MAGE-A4 HLA class I binding peptide can be used in antigen presenting cells which express an HLA-B*3701 molecule. As used herein, "a HLA-B37 molecule" includes the subtypes HLA-B*3701, B*3702, B*3703N, B*3704, and B*3705. HLA-B37 molecules may also include subtypes which can be found in Bodmer et al., *Tissue Antigens* 49:297, 1996 or *The HLA FactsBook*, S. G. E. Marsh, P. Parham, L. D. Barber (Academic Press, 2000). A listing of presently identified HLA-B37 subtypes can be found on the European Bioinformatics Institute website, in the IMGT/HLA database at internet URL http://www.ebi-.ac.uk/imgt/hla/.

It will also be understood that the invention embraces the use of the sequences in expression vectors including recombinant plasmids, phagemids, viruses and the like, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. Delivery of expression vectors containing the MAGE-A4 sequences in vivo and/or in vitro can be via the use of nucleic acid delivery systems known in the art (see, e.g., Allsopp et al., *Eur. J. Immunol.* 26(8):1951–1959, 1996). Recombinant vectors including viruses selected from the group consisting of adenoviruses, adeno-associated viruses, poxviruses including vaccinia viruses and attenuated poxviruses such as NYVAC, Semliki Forest virus, Venezuelan equine encephalitis virus, retroviruses, Sindbis virus, and Ty virus-like particle, plasmids (e.g. "naked" DNA), bacteria (e.g. the bacterium Bacille Calmette Guerin, BCG), and the like can be used in such delivery, for example, for use as a vaccine. Other viruses, expression vectors and the like which are useful in preparation of a vaccine are known to one of ordinary skill in the art. One can test the MAGE-A4 delivery systems in standard model systems such as mice to determine efficacy of the delivery system. The systems also can be tested in human clinical trials.

In addition, non-MAGE-A4 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in MAGE-A4 compositions and vaccines.

Especially preferred are nucleic acids encoding a series of epitopes, known as "polytopes". The epitopes can be arranged in sequential or overlapping fashion (see, e.g., Thomson et al., *Proc. Natl. Acad. Sci. USA* 92:5845–5849, 1995; Gilbert et al., *Nature Biotechnol.* 15:1280–1284, 1997), with or without the natural flanking sequences, and can be separated by unrelated linker sequences if desired. The polytope is processed to generated individual epitopes which are recognized by the immune system for generation of immune responses.

Thus, for example, MAGE-A4 HLA binding peptides such as SEQ ID NOs:3, 4, 5, 6, 8 and 9, which are presented by MHC molecules and recognized by CTLs (or T helper lymphocytes) can be combined with other peptides from tumor rejection antigens (e.g. by preparation of hybrid nucleic acids or polypeptides) to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, GAGE-9, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, MAGE-C3, MAGE-C4, MAGE-C5, NY-ESO-1, LAGE-1, SSX-1, SSX-2 (HOM-MEL-40), SSX-4, SSX-5, SCP-1, CT7, CT9 and CT10. For example, antigenic peptides characteristic of tumors include those listed in Table 3 below.

TABLE 3

Exemplary Antigens

| Gene | MHC | Peptide | Position | SEQ ID NO: |
|---|---|---|---|---|
| MAGE-A1 | HLA-A1 | EADPTGHSY | 161–169 | 11 |
| | HLA-Cw16 | SAYGEPRKL | 230–238 | 12 |
| MAGE-A3 | HLA-A1 | EVDPIGHLY | 168–176 | 13 |
| | HLA-A2 | FLWGPRALV | 271–279 | 14 |
| | HLA-B44 | MEVDPIGHLY | 167–176 | 15 |
| BAGE | HLA-Cw16 | AARAVFLAL | 2–10 | 16 |
| GAGE-1,2 | HLA-Cw16 | YRPRPRRY | 9–16 | 17 |
| RAGE | HLA-B7 | SPSSNRIRNT | 11–20 | 18 |
| GnT-V | HLA-A2 | VLPDVFIRC(V) | 2–10/11 | 19, 20 |
| MUM-1 | HLA-B44 | EEKLIVVLF | exon 2/intron | 21 |
| | | EEKLSVVLF (wild type) | | 22 |
| CDK4 | HLA-A2 | ACDPHSGHFV | 23–32 | 23 |
| | | ARDPHSGHFV (wild type) | | 24 |
| β-catenin | HLA-A24 | SYLDSGIHF | 29–37 | 25 |
| | | SYLDSGIHS (wild type) | | 26 |
| Tyrosinase | HLA-A2 | MLLAVLYCL | 1–9 | 27 |
| | HLA-A2 | YMNGTMSQV | 369–377 | 28 |
| | HLA-A2 | YMDGTMSQV | 369–377 | 44 |
| | HLA-A24 | AFLPWHRLF | 206–214 | 29 |
| | HLA-B44 | SEIWRDIDF | 192–200 | 30 |
| | HLA-B44 | YEIWRDIDF | 192–200 | 31 |
| | HLA-DR4 | QNILLSNAPLGPQFP | 56-70 | 32 |
| | HLA-DR4 | DYSYLQDSDPDSFQD | 448-462 | 33 |
| Melan-A[MART-1] | HLA-A2 | (E)AAGIGILTV | 26/27–35 | 34, 35 |
| gp100[Pmel117] | HLA-A2 | ILTVILGVL | 32–40 | 36 |
| | HLA-A2 | KTWGQYWQV | 154–162 | 37 |
| | HLA-A2 | ITDQVPFSV | 209–217 | 38 |
| | HLA-A2 | YLEPGPVTA | 280–288 | 39 |
| | HLA-A2 | LLDGTATLRL | 457–466 | 40 |
| | HLA-A2 | VLYRYGSFSV | 476–485 | 41 |
| PRAME | HLA-A24 | LYVDSLFFL | 301–309 | 42 |
| MAGE-A6 | HLA-Cw16 | KISGGPRISYPL | 292–303 | 43 |
| NY-ESO-1 | HLA-A2 | SLLMWITQCFL | 157–167 | 45 |
| | HLA-A2 | SLLMWITQC | 157–165 | 46 |
| | HLA-A2 | QLSLLMWIT | 155–163 | 47 |

Other examples of HLA class I and HLA class II binding peptides will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more MAGE-A4 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Natl. Acad. Sci USA* 92(13):5845–5849, 1995; Gilbert et al., *Nature Biotechnol.* 15(12):1280–1284, 1997; Thomson et al., *J. Immunol.* 157 (2):822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As it has been found that human HLA-B37 molecules present a MAGE-A4 immunogenic polypeptide, the expression vector may also include a nucleic acid sequence coding for an HLA-B37 molecule. Nucleic acids encoding single chain soluble HLA/peptide complex including a MAGE-A4 immunogenic polypeptide fused to an HLA-B37 molecule can be prepared as described by Lone et al. (*J. Immunother.* 21:283–294, 1998).

In a situation where the vector contains both coding sequences, it can be used to transfect a cell which does not normally express either one. The MAGE-A4 immunogenic polypeptide coding sequence may be used alone, when, e.g. the host cell already expresses an HLA-B37 molecule. Of course, there is no limit on the particular host cell which can be used as the vectors which contain the two coding sequences may be used in host cells which do not express HLA-B37 molecules if desired, and the nucleic acid coding for the MAGE-A4 immunogenic polypeptide can be used in antigen presenting cells which express an HLA-B37 molecule.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids, bacteria and virus genomes as disclosed herein, such as adenovirus, poxvirus and BCG. A cloning vector is one which is able to replicate in a host cell or be replicated after its integration into the genome of a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. As noted above, certain preferred nucleic acids express only fragments of MAGE-A4 polypeptides which include the HLA binding peptides described herein.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a MAGE-A4 immunogenic polypeptide. That heterologous DNA (RNA) is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus to express proteins for immunization is disclosed by Warnier et al., in intradermal injection in mice for immunization against P1A (*Int. J. Cancer*, 67:303–310, 1996).

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. First, the invention permits the artisan to diagnose a disorder characterized by expression of a MAGE-A4 immunogenic polypeptide. These methods involve determining expression of a MAGE-A4 HLA binding peptide, or a complex of a MAGE-A4 HLA binding peptide and an HLA class I molecule in a biological sample. The expression of a peptide or complex of peptide and HLA class I molecule can be determined by assaying with a binding partner for the peptide or complex, such as an antibody. The expression of MAGE-A4 in a biological sample, such as a tumor biopsy, can also be tested by standard PCR amplification protocols using MAGE-A4 primers, such as fragments of SEQ ID NO:1.

Preferably, the diagnostic methods involve contacting a biological sample isolated from a subject with an agent specific for the MAGE-A4 HLA binding peptide to detect the presence of the MAGE-A4 HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and MAGE-A4 HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a tissue in vivo and the agent specific for the MAGE-A4 immunogenic polypeptide can be used to detect the presence of such molecules in the tissue. Alternatively, the biological sample can be located in vitro (e.g., a blood sample, tumor biopsy, tissue extract). In a particularly preferred embodiment, the biological sample can be a cell-containing sample, more preferably a sample containing tumor cells.

The invention further includes nucleic acid or protein microarrays which include MAGE-A4 HLA binding peptides or nucleic acids encoding such peptides. In this aspect of the invention, standard techniques of microarray technology are utilized to assess expression of the MAGE-A4 HLA binding peptides and/or identify biological constituents that bind such peptides. In one embodiment, a microarray of functional variant peptides can be used to assess binding to HLA-B37 molecules contacted with the microarray. The constituents of biological samples include antibodies, HLA molecules, lymphocytes (particularly T lymphocytes), and the like. Microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485):1760–1763, 2000. Nucleic acid arrays, particularly arrays of aptamers that bind MAGE-A4 HLA binding peptides also can be used for diagnostic applications, such as for identifying subjects that have a condition characterized by MAGE-A4 HLA binding peptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

In some embodiments, one or more control peptide or nucleic acid molecules are attached to the substrate. Preferably, control nucleic acid molecules allow determination of factors such as binding characteristics, reagent quality and effectiveness, hybridization success, and analysis thresholds and success.

The invention also permits the artisan to treat a subject having a disorder characterized by expression of a MAGE-A4 immunogenic polypeptide. Treatments include administering an agent which enriches in the subject a complex of a MAGE-A4 HLA binding peptide and an HLA class I molecule, and administering CD8+ T lymphocytes which are specific for such complexes. Agents useful in the foregoing treatments include MAGE-A4 immunogenic polypeptides and functional variants thereof, complexes of such peptides and HLA class I binding molecules (e.g., HLA-B*3701), antigen presenting cells bearing complexes of a MAGE-A4 immunogenic polypeptide and an HLA class I binding molecule, soluble single chain fusions of HLA and MAGE-A4 polypeptides, and the like. The invention also permits an artisan to selectively enrich a population of T lymphocytes for CD8+ T lymphocytes-specific for a MAGE-A4 HLA binding peptide.

The isolation of the MAGE-A4 HLA binding peptides also makes it possible to isolate or design nucleic acids which encode the MAGE-A4 HLA binding peptides. Nucleic acids can be used to produce in vitro or in prokaryotic or eukaryotic host cells the MAGE-A4 HLA binding peptides or proteins containing such peptides. A variety of methodologies well-known to the skilled practitioner can be utilized to obtain isolated MAGE-A4 HLA binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the MAGE-A4 HLA binding peptides of the invention may also be synthesized in vitro. Those skilled in the art also can readily follow known methods for isolating peptides in order to obtain isolated MAGE-A4 HLA binding peptides. These include, but are not limited to, immunochromotography, HPLC, size-exclusion chromatography, ion-exchange chromatography and immune-affinity chromatography.

These isolated MAGE-A4 HLA binding peptides, or complexes of the peptides and HLA class I molecules, such as an HLA-B*3701 molecule, may be combined with materials such as adjuvants to produce vaccines useful in treating disorders characterized by expression of the MAGE-A4 immunogenic polypeptide. In addition, vaccines can be prepared from cells which present the MAGE-A4 HLA binding peptide/HLA complexes on their surface, such as transfected dendritic cells, transfected B cells, non-proliferative transfectants, etcetera. In all cases where cells are used as a vaccine, these can be cells transfected with coding sequences for one or both of the components necessary to stimulate CD8+ lymphocytes, or be cells which already express both molecules without the need for transfection. Vaccines also encompass expression vectors and naked DNA or RNA, encoding a MAGE-A4 HLA binding peptide, precursors thereof, or fusion proteins thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993).

The MAGE-A4 HLA binding peptides, as well as complexes of MAGE-A4 HLA binding peptides and HLA molecules, also may be used to produce antibodies, using standard techniques well known to the art. Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and an appropriate HLA class I molecule, and the like to an animal to induce polyclonal antibodies. The production of monoclonal antibodies is according to techniques well known in the art.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody, i.e., in the present invention, the ability to bind a MAGE-A4 HLA-B*3701 binding peptide or a complex of such a peptide with an HLA molecule. However, using certain methods of humanization, the affinity and/or specificity of binding of the antibody may be increased using methods of "directed evolution", as described by Wu et al., *J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies and human monoclonal antibodies, such as those produced by mice having functional human immunoglobulin gene loci.

Such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin or bacterial toxins, other cytostatic or cytolytic drugs, and so forth, for therapeutic purposes. Antibodies prepared according to the invention also preferably are specific for the peptide/HLA complexes described herein.

When "disorder" or "condition" is used herein, it refers to any pathological condition where the MAGE-A4 immunogenic polypeptide is expressed. Such disorders include cancers, including bladder carcinomas, melanomas, esophageal carcinomas, lung carcinomas, head and neck carcinomas, breast carcinomas, colorectal carcinomas, hepatocellular carcinomas, leukemias, myelomas, rhabdomyosarcomas, sarcomas and renal carcinomas.

Some therapeutic approaches based upon the disclosure are premised on inducing a response by a subject's immune system to MAGE-A4 immunogenic polypeptide presenting cells. One such approach is the administration of autologous CD8$^+$ T cells specific to the complex of a MAGE-A4 HLA binding peptide and an HLA class I molecule to a subject with abnormal cells of the phenotype at issue. It is within the skill of the artisan to develop such CD8$^+$ T cells in vitro. Generally, a sample of cells taken from a subject, such as blood cells, are contacted with a cell presenting the complex and capable of provoking CD8$^+$ T lymphocytes to proliferate. The target cell can be a transfectant, such as a transfected COS cell, or a transfected antigen presenting cell bearing HLA class I molecules, such as dendritic cells or B cells. These transfectants present the desired complex of their surface and, when combined with a CD8$^+$ T lymphocyte of interest, stimulate its proliferation. COS cells, are widely available, as are other suitable host cells. The clonally expanded autologous CD8$^+$ T lymphocytes then are administered to the subject. The CD8$^+$ T lymphocytes then stimulate the subject's immune response, thereby achieving the desired therapeutic goal.

Another method for selecting antigen-specific CTL clones has recently been described (Altman et al., *Science* 274: 94–96, 1996; Dunbar et al., *Curr. Biol.* 8:413–416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, *J. Immunol.* 136(5): 1917, 1986; Riddel et al., *Science* 257: 238, 1992; Lynch et al, *Eur. J. Immunol.* 21: 1403–1410, 1991; Kast et al., *Cell* 59: 603–614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a tumor associated gene sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a tumor associated gene derived TRA is being presented, and the subject is an appropriate candidate for the therapeutic approaches set forth supra.

Adoptive transfer is not the only form of therapy that is available in accordance with the invention. $CD8^+$ T lymphocytes can also be provoked in vivo, using a number of approaches. One approach is the use of non-proliferative cells expressing the complex. The cells used in this approach may be those that normally express the complex, which could be dendritic cells or cells transfected with one or both of the genes necessary for presentation of the complex. Chen et al., (*Proc. Natl. Acad. Sci. USA* 88: 110–114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a MAGE-A4 HLA binding peptide may be operably linked to promoter and enhancer sequences which direct expression of the MAGE-A4 HLA binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding MAGE-A4 HLA binding peptides. Nucleic acids encoding a MAGE-A4 HLA binding peptide also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials de facto "infect" host cells. The cells which result present the complex of interest, and are recognized by autologous $CD8^+$ T cells, which then proliferate.

A similar effect can be achieved by combining a MAGE-A4 HLA binding peptide with an adjuvant to facilitate incorporation into HLA class I presenting cells in vivo. If larger than the HLA class I binding portion, the MAGE-A4 HLA binding peptide can be processed if necessary to yield the peptide partner of the HLA molecule while the TRA is presented without the need for further processing. Generally, subjects can receive an intradermal injection of an effective amount of the MAGE-A4 immunogenic polypeptide. Initial doses can be followed by booster doses, following immunization protocols standard in the art.

As part of certain immunization compositions, one or more cancer associated antigens or stimulatory fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillaja saponaria* extract; DQS21, described in PCT application WO96/33739 (SmithKline Beecham); QS-7, QS-17, QS-18, and QS-L1 (So et al., *Mol. Cells* 7:178–186, 1997); incomplete Freund's adjuvant; complete Freund's adjuvant; montanide; immunostimulatory oligonucleotides (see e.g. CpG oligonucleotides described by Kreig et al., *Nature* 374:546–9, 1995); and various water-in-oil emulsions prepared from biodegradable oils such as squalene and/or tocopherol. Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432–1434, 1995), GM-CSF and IL-18. Thus cytokines can be administered in conjunction with antigens and adjuvants to increase the immune response to the antigens.

There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284–6289, 1998).

B7 typically is not expressed on tumor cells so they are not efficient antigen presenting cells (APCs) for T cells.

Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). Tumor cell transfection with B7 has been discussed in relation to in vitro CTL expansion for adoptive transfer immunotherapy by Wang et al. (*J. Immunother.* 19:1–8, 1996). Other delivery mechanisms for the B7 molecule would include nucleic acid (naked DNA) immunization (Kim et al., *Nature Biotechnol.* 15:7:641–646, 1997) and recombinant viruses such as adeno and pox (Wendtner et al., *Gene Ther.* 4:726–735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263–266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637–642, 1997; Fenton et al., *J. Immunother.*, 21:95–108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2(B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be oral, intravenous, intraperitoneal, intramuscular, intranasal, intracavity, subcutaneous, intradermal or transdermal.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the MAGE-A4 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Example 1

Identification of HLA Class I Binding Peptides of MAGE-A4

Cel Lines, Media, and Reagents

The Epstein Barr Virus-transformed B (EBV-B) cell lines and the melanoma cell lines were cultured in IMDM supplemented with 10% FCS. 293-EBNA cells were maintained in DMEM supplemented with 10% FCS. All culture media were purchased from GibcoBRL (Paistey, UK) and supplemented with 0.24 mM L-asparagine, 0.55 mM L-arginine, 1.5 mM L-glutamine (AAG), 100 U/ml penicillin, and 100 µg/ml streptomycin. Cell line MZ2-MEL 2.2-MAGE-A4 was obtained by co-transfecting into MZ2-MEL 2.2 a pcD-NAI/Amp plasmid (Invitrogen) that contains the coding sequence of MAGE-A4 together with vector pSvtkneoβ, which contains the coding sequence conferring resistance to geneticin (13). Human recombinant IL-2 was purchased from Eurocetus (Amsterdam, The Netherlands). IL-7 was purchased from Genzyme (Cambridge, Mass.), GM-CSF (Leucomax) from Schering-Plough (Brinny, Ireland) and IFN-γ from Peprotech (Rocky Hill, USA). Human recombinant IL-4, IL-6, and IL-12 were produced in our laboratory. 1 U/ml of IL-6 is the concentration needed to obtain half-maximal proliferation of mouse 7TD1 cells (14). Geneticin was purchased from GibcoBRL.

Recombinant Viruses and Infection of Cell Lines

The recombinant canarypox ALVAC-MAGE-A4, the vaccinia-MAGE-A4 and the parental vaccinia viruses were provided by Aventis Pasteur (Lyon, France). Retroviral vector MAGE-A4-CSM encodes the full length MAGE-A4 protein and the truncated form of the human low affinity nerve growth factor receptor (LNGFr). It was produced as previously reported (15). EBV-B cells were transduced by co-culture with irradiated packaging cell lines producing the MAGE-A4-CSM vector in the presence of polybrene (8 µg/ml). After 72 hours, lymphocytes were harvested and seeded in fresh medium. The percentage of infected cells was evaluated 48 hours later by flow cytometry for LNGFr expression with the mAb 20.4 (ATCC, Rockville, Md.). The LNGFr positive cells were purified by magnetic cell sorting using rat anti-mouse IgGI-coated beads (Dynabeads M-450, DYNAL A.S. N012 Oslo, Norway). Using the same protocol, melanoma cell lines AVL3-MEL and LB 1751-MEL were transduced with retroviral vector B37-CSM, that codes for the HLA-B*3701 molecule and the truncated form of LNGFr.

Dendritic Cells and CD8+ Responder T Cells

Peripheral blood was obtained from hemochromatosis patient LB2257 as standard buffy coat preparations, which were laid down on a 15-ml Lymphoprep layer (Axis-Shield PoCAS, Oslo, Norway) in 50-ml tubes. To minimize contamination of the PBMCs by platelets, the tubes were first centrifuged at 1,000 rpm for 20 min at room temperature. After removal of the top 20–25 ml, containing most of the platelets, the tubes were centrifuged at 1,500 rpm for 20 min at room temperature. The interphase containing the PBMCs was harvested and washed three times (or more) in cold phosphate buffer solution with 2 mM EDTA in order to eliminate the remaining platelets. To generate autologous dendritic cells, PBMCs were depleted from T lymphocytes by rosetting with sheep erythrocytes (Bio Mérieux, Marcyl'Etoile, France) treated with 2-aminoethylisothiouronium (Sigma-Aldrich, Steinheim, Germany). Rosetted T cells were treated with $NH_4Cl$ (160 mM) to lyse the sheep erythrocytes and washed. $CD8^+$ T lymphocytes were isolated from rosetted T cells by positive selection using an anti-CD8 mAb coupled to magnetic microbeads (Miltenyi Biotec, Bergisch Gladbach, Germany). They were then sorted through a magnet and subsequently frozen. The day before the co-culture with dendritic cells, $CD8^+$ T cells were thawed and grown overnight in IMDM supplemented with 10% human serum, AAG, and antibiotics (hereafter referred to as complete IMDM) in the presence of 5 U/ml of IL-2. The lymphocyte-depleted PBMCs were left to adhere for 1 h at 37° C. in culture flasks (FALCON, Becton Dickinson) at a density of $10^6$ cells per $cm^2$ in RPMI 1640 supplemented with Hepes (2.38 g/liter), AAG, antibiotics, and 10% FCS (hereafter referred to as complete RPMI medium). Nonadherent cells were discarded and adherent cells were cultured in the presence of IL-4 (200 U/ml) and GM-CSF (70 ng/ml) in complete RPMI medium. Cultures were fed on days 2 and 4 by removing ⅓ of the volume and adding fresh medium with IL-4 (200 U/ml) and GM-CSF (70 ng/ml). They were frozen on day 6.

Mixed Lymphocyte-Dendritic Cell Culture

Dendritic cells ($4 \times 10^6$) were infected with ALVAC-MAGE-A4 at a multiplicity of infection (MOI) of 30 in 200 µl of complete RPMI medium at 37° C. under 5% $CO_2$. The infected dendritic cells were washed after 2 h. Autologous responder CD8+ T lymphocytes ($1.5 \times 10^5$) were mixed with infected dendritic cells ($3 \times 10^4$) in U-bottomed microwells in 200 µl of complete IMDM in the presence of IL-6 (1,000 U/ml) and IL-12 (10 ng/ml). On days 6 and 13, autologous dendritic cells were thawed and infected the day after with ALVAC-MAGE-A4. The infected cells were used to restimulate the responder lymphocytes in medium supplemented with IL-2 (10 U/ml) and IL-7 (5 ng/ml). The responder lymphocytes were assessed on day 21 for their capacity to lyse autologous EBV-B cells infected with vaccinia-MAGE-A4.

Cytotoxicity Assay

The cytotoxicity of an aliquot of each microculture was tested on autologous EBV-B cells infected with either vaccinia-MAGE-A4 or the parental vaccinia virus. Infection was performed on $2 \times 10^6$ target cells for 2 h at an MOI of 20 in 150 µl of complete RPMI medium. Infected cells were washed, labeled with 100 µCi of $Na(^{51}Cr)O_4$, and added to the responder cells at an effector/target (E:T) ratio of 40:1. Unlabeled K562 cells were also added ($5 \times 10^4$ per V-bottom microwell) to block NK activity. Individual microcultures were tested on each target in duplicate. Chromium release was measured after incubation at 37° C. for 4 h. The melanoma cell lines were labeled with $Na(^{51}Cr)O_4$ as described above and pulsed, if indicated, for 15 min with 1 µg/ml of peptide.

Isolation of CD8+ T Cell Clone Specific for MAGE-A4

T cells from the microculture with anti-MAGE-A4 reactivity were cloned in U-bottomed microplates by limiting dilution in complete IMDM supplemented with IL-2 (50 U/ml) and 15 µg/ml gentamicin using, as stimulators, irradiated (100 Gy) 5–15×10³ autologous EBV-B cells transduced with a retrovirus coding for MAGE-A4. Allogeneic EBV-B cells (5–15×10³ irradiated LG2-EBV-B cells per well) were used as feeder cells. Established CTL clones were grown in complete IMDM supplemented with IL-2 (50 U/ml) and 3×10⁵ CTL were passaged weekly with irradiated feeder cells (1.5×10⁶ LG2 EBV-B cells per well in a 24-well plate) and irradiated autologous EBV-B cells transduced with a retrovirus coding for MAGE-A4 (10⁵ cells per well).

Transfection of 293-EBNA Cells and TNF Assay

293-EBNA cells (2×10⁴) were distributed in flat-bottom microwells and cotransfected with pcDNAI/Amp containing the MAGE-A4 cDNA (50 ng) and 50 ng of pcDNAI/Amp containing the coding sequences of each of the five putative HLA alleles using 1 µl of Lipofectamine (GibcoBRL). Transfected cells were incubated for 24 h at 37° C. and 8% $CO_2$. The transfectants were then tested for their ability to stimulate the production of TNF by the CTL clone. Briefly, 5,000 CTL were added to the microwells containing the transfectants, in a total volume of 100 µl of complete IMDM supplemented with 25 U/ml of IL-2. After 24 h, the supernatant was collected and its TNF content was determined by testing its cytotoxic effect on WEHI-164 clone 13 cells in a MTT colorimetric assay (13, 16, 17).

Peptide Recognition Assay

Peptides were synthesized on solid phase using Fmoc for transient $NH_2$-terminal protection and were characterized using mass spectrometry. All peptides were >90% pure, as indicated by analytical HPLC. Lyophilized peptides were dissolved at 2 mg/ml in 10 mM acetic acid and 10% DMSO, and stored at −20° C. The first screening was performed with autologous EBV-B cells incubated with 16 amino-acid long peptides at a concentration of 1 µg/ml. Peptide-pulsed targets were tested for recognition by CTL at an E:T ratio of 5:1.

Isolation of an Anti-MAGE-A4 CTL Clone

Monocyte-derived dendritic cells of blood donor LB2257 were infected with an avian poxvirus, ALVAC, carrying the MAGE-A4 coding sequence (ALVAC-MAGE-A4). These antigen-presenting cells were distributed in 96 microwells and used to stimulate autologous CD8⁺ T lymphocytes in the presence of IL-6 and IL-12. After two weekly restimulations with dendritic cells infected with ALVAC-MAGE-A4 in the presence of IL-2 and IL-7, responder cells were tested on day 21 for their specific lytic activity on autologous EBV-B cells infected with a vaccinia poxvirus encoding MAGE-A4 (vaccinia-MAGE-A4). The reason for using vaccinia instead of ALVAC was that EBV-B cells infected with ALVAC are poor targets for cytotoxicity assays (data not shown). EBV-B cells infected with the parental vaccinia were used as control targets because CTL can recognize antigens shared by ALVAC and vaccinia poxvirus (18).

One microculture with anti-MAGE-A4 lytic activity was obtained. The responder lymphocytes were cloned by limiting dilution using, as stimulator cells, autologous EBV-B cells transduced with a retrovirus carrying the coding sequence of MAGE-A4. This new stimulation combination was used to stimulate the anti-MAGE-A4 CTL, while avoiding restimulating CTL directed against poxvirus antigens. A stable CTL clone LB2257 661/F2 (hereafter referred to as CTL F2) was obtained, which lysed EBV-B cells infected with vaccinia-MAGE-A4 but not EBV-B cells infected with the parental vaccinia (FIG. 1).

Identification of the HLA Presenting Molecule

Figure 2:
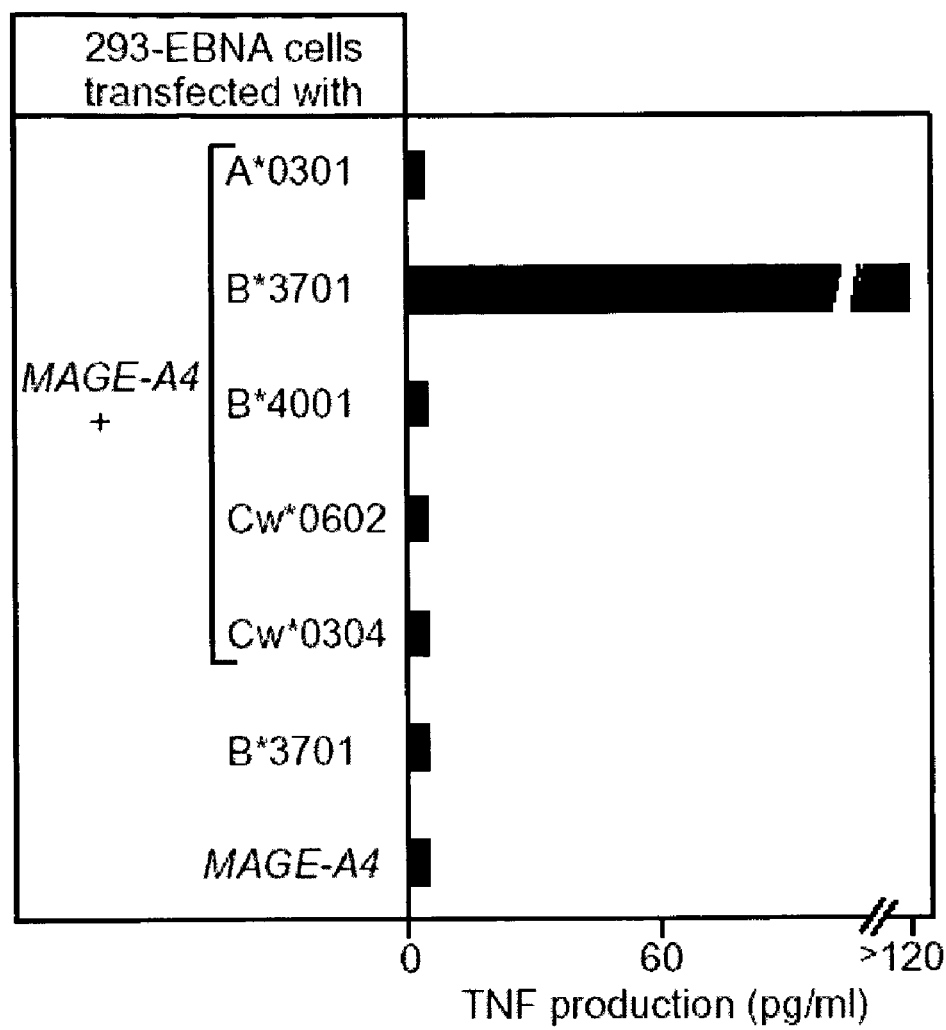
FIG. 2 shows that the MAGE-A4 antigenic peptide is presented by HLA-B37 molecules. 293-EBNA cells were transiently transfected with a MAGE-A4 cDNA and each of the cDNAs coding for putative HLA-presenting molecules. The cDNAs were inserted in expression vector pcDNAI/Amp. Transfections were performed in microwells with 20,000 293-EBNA cells, 50 ng of each cDNA and 1 μl of Lipofectamine. One day after transfection, 5,000 CTL F2 were added to the transfected cells. TNF production was measured after overnight co-culture by testing the toxicity of the supernatants for TNF-sensitive WEHI 164 clone 13 cells.

Blood donor LB2257 was typed HLA-A*0301, B*3701, B*4001, Cw*0302 and Cw*0602. To identify the HLA molecule that presents the MAGE-A4 peptide recognized by CTL F2, 293-EBNA cells, which are derived from a human embryonic kidney cell line, were transiently transfected with a MAGE-A4 cDNA containing the full length MAGE-A4 open reading frame (SEQ ID NO:1; see GenBank accession number U10687) together with each of the cDNAs encoding the putative HLA presenting molecules. Only those cells that were transfected with MAGE-A4 and HLA B*3701 stimulated CTL F2 to produce TNF (FIG. 2).

Identification of the Antigenic Peptide

Figure 3A:
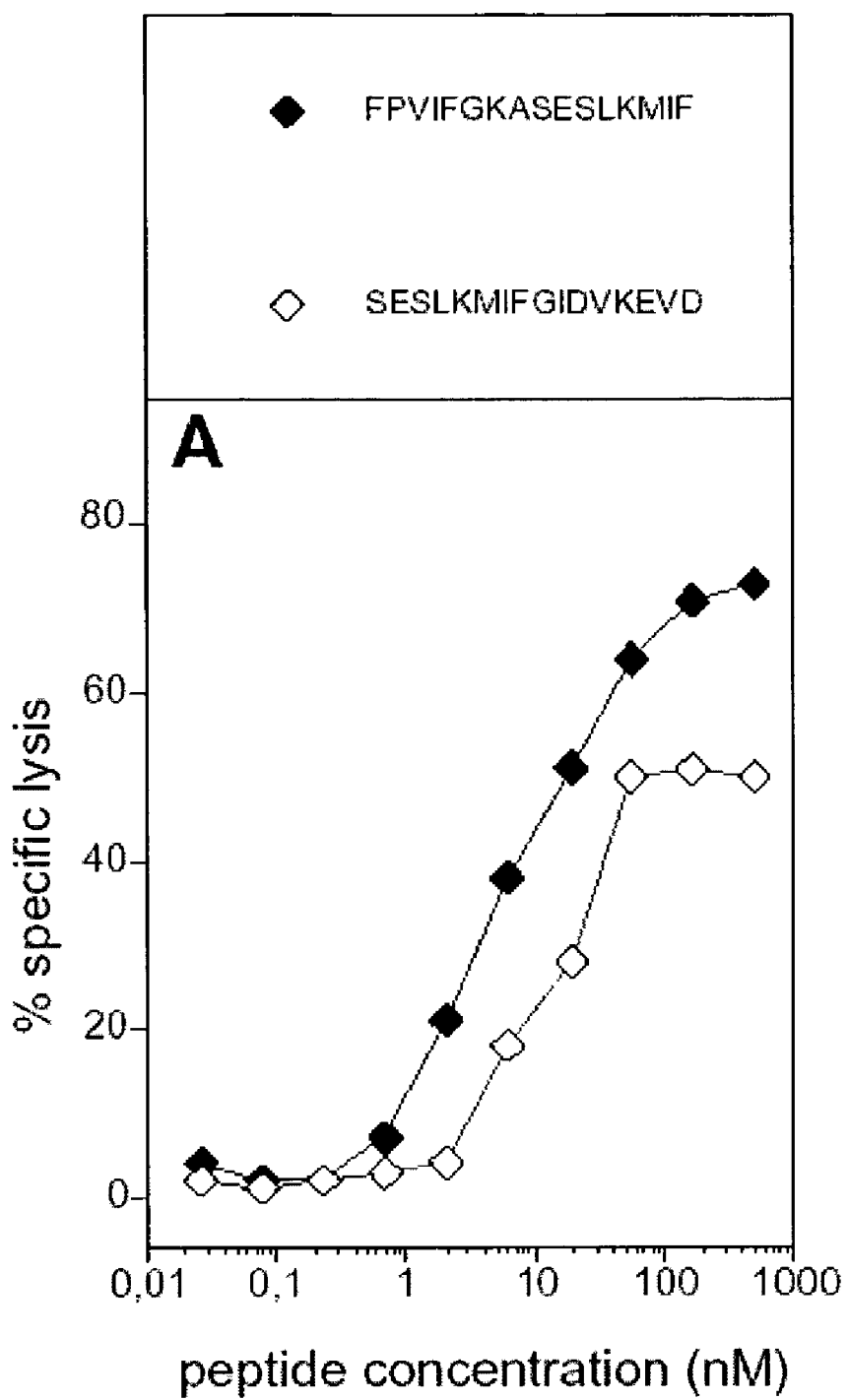
FIG. 3A shows identification of two 16-mer peptides (FPVIFGKASESLKMIF, SEQ ID NO:3; SESLKMIFGIDVKEVD, SEQ ID NO:4) recognized by CTL F2.
Figure 3B:
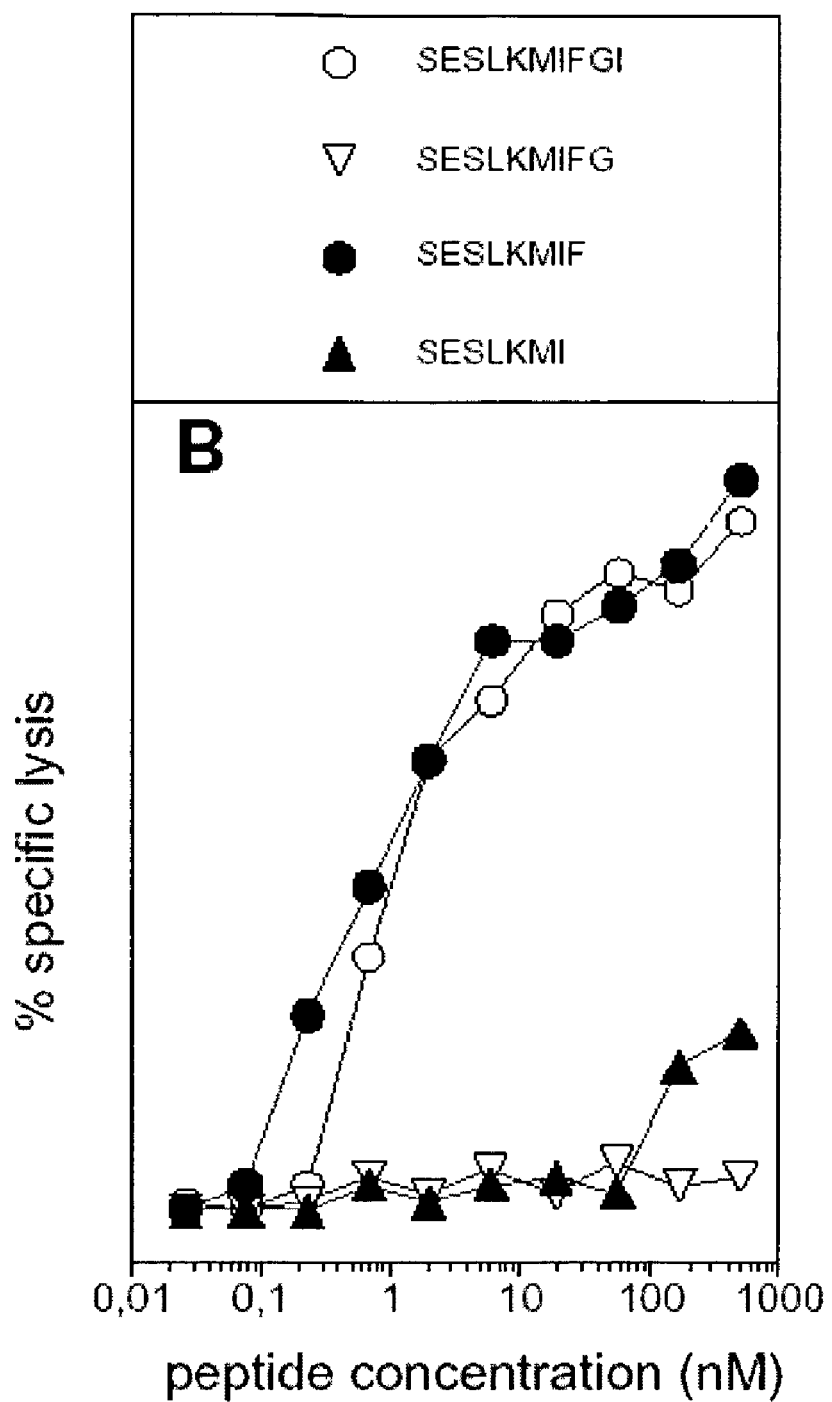
FIG. 3B shows identification of the shortest peptide recognized by CTL F2 (SESLKMIFGI, SEQ ID NO:5; SESLKMIF, SEQ ID NO:6).

To determine the peptide recognized by CTL F2, we screened a set of peptides covering the entire MAGE-A4 protein sequence. These 16 amino-acid long peptides overlapped by 12 residues. Autologous EBV-B cells were incubated with 1 µg/ml of each of these peptides and tested for lysis by CTL F2. Peptide FPVIFGKASESLKMIF (MAGE-A4$_{148-163}$; SEQ ID NO:3) and SESLKMIFGIDVKEVD (MAGE-A4$_{156-171}$; SEQ ID NO:4) scored positive (FIG. 3A). The consensus anchor residues for HLA-B37 are D/E in position 2, F/M/L in position 8 and I/L in the C-terminal position (19, 20). One peptide, SESLKMIFGI (SEQ ID NO:5), contains these three anchor residues but its sequence was only included in one of the two long peptides that scored positive. A number of peptides of different lengths were therefore tested. Peptide SESLKMIFGI (SEQ ID NO:5) and peptide SESLKMIF (SEQ ID NO:6) scored positive and half maximal lysis of autologous EBV-B target cells was obtained at a peptide concentration of 1 nM (FIG. 3B). This is within the range of the previously identified MAGE antigenic peptides, for which values ranging from 0.05 to 100 nM were observed (18, 21–24). These two peptides are encoded by both MAGE-A4a and MAGE-A4b.

Figure 3C:
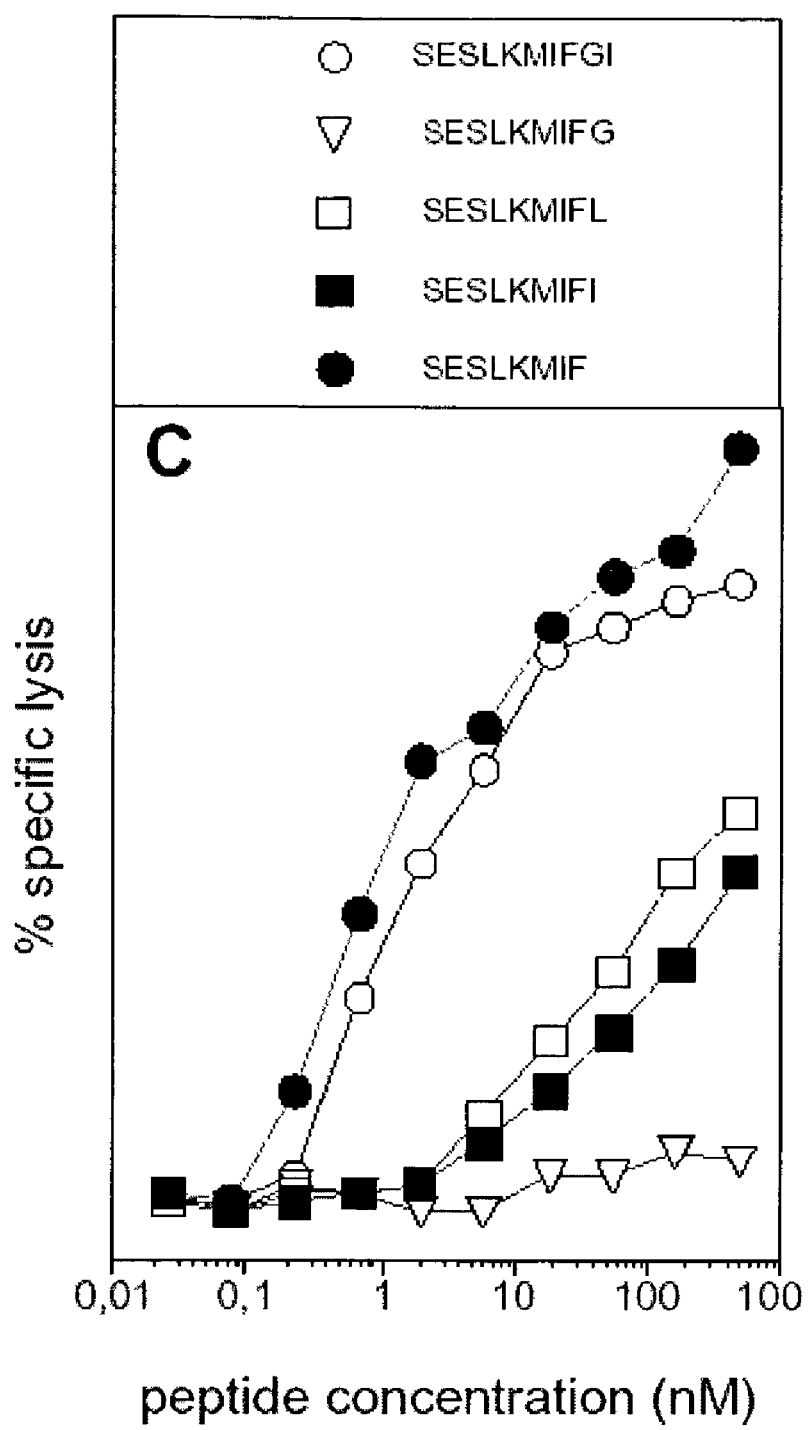
FIG. 3C shows a test of peptides modified at the C-terminus. Autologous EBV-B cells were $^{51}$Cr-labeled and incubated for 15 min with 3-fold dilutions of synthetic peptides (SESLKMIFI, SEQ ID NO:8; SESLKMIFL, SEQ ID NO:9). Autologous CTL F2 was subsequently added at an effector-to-target ratio of 5:1. Chromium release was measured after 4 h. The concentrations indicated in the figure are the concentrations during the 4 h of incubation. Experiments described in FIG. 3B and FIG. 3C were performed with HPLC purified peptides (99% pure).

Interestingly, nonapeptide SESLKMIFG (SEQ ID NO:7) was not recognized by CTL F2 (FIG. 3B). The C-terminal residue G was replaced by a consensus anchor residue for B37 (19), either a I (SESLKMIFI; SEQ ID NO:8) or a L (SESLKMIFL; SEQ ID NO:9). Targets pulsed with a very high and most probably not physiological concentration of these two modified peptides were recognized by the CTL (FIG. 3C). The results suggested that the C-terminal residue is very important for the binding to B37 and that the presence of a G decreases the affinity of the peptide for B37.

Lysis of Tumor Cell Lines

Figure 4:
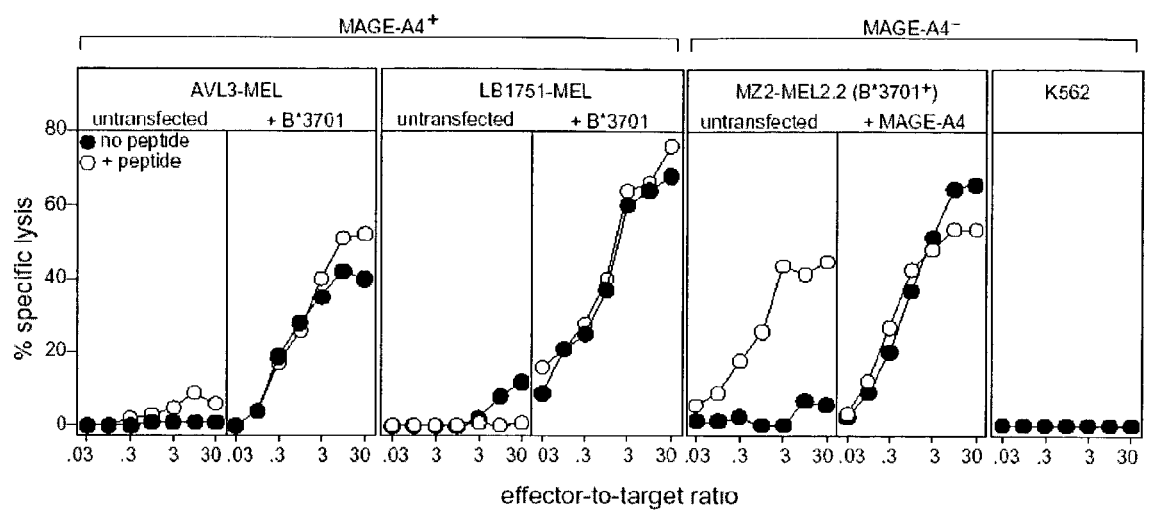
FIG. 4 shows lysis by CTL F2 of B*3701 tumor cell lines expressing MAGE-A4. Target cells were $^{51}$Cr-labeled and, if indicated, pulsed for 15 min with 1 μg/ml of peptide SESLKMIF (SEQ ID NO:6). The cells were then incubated for 4 h with CTL F2 at the indicated effector-to-target ratios. Chromium release was measured after 4 h.

Since we used dendritic cells expressing MAGE-A4 to activate CTL F2, it was important to verify that tumor cells also process the MAGE-A4 antigen. Because we had no tumor cell lines expressing both MAGE-A4 and B*3701, we transduced MAGE-A4-expressing melanoma cell lines with a retrovirus carrying the B*3701 coding sequence. The B*3701-transduced cell lines were both lysed by CTL F2 (FIG. 4). Melanoma cell line MZ2-MEL.2.2, which expressed B*3701 but not MAGE-A4, was transduced with a retrovirus carrying the MAGE-A4 coding sequence. It was efficiently lysed after transduction (FIG. 4). Control K562 cells were not lysed.

The new MAGE-A4 antigenic peptide described here is presented by B*3701 molecules. The HLA allelic group B37 comprises five alleles. B*3701 corresponds to the B37 serological specificity, but B*3702 is not recognized by serum antibodies and it is therefore considered as "blank". However it is possible that HLA-B*3702, as well as other HLA-B37 alleles (e.g., B*3703N, B*3704, B*3705), also are able to present the peptide described herein. B37 molecules are rarely expressed in the different major ethnic groups: Black (2%), Caucasoid (3%), Oriental (2%), Amerindian (4%). Identification of additional MAGE-A4 antigenic peptides will be important because a number of tumors express MAGE-A4 without expressing MAGE-A1 and MAGE-A3. It is the case for carcinomas of the lung (15%), the head and neck (14%), the esophagus (11%), and the bladder (10%).

REFERENCES

1. De Plaen E, Arden K, Traversari C et al. Structure, chromosomal localization and expression of twelve genes of the MAGE family. *Immunogenetics* 1994: 40: 360–9.
2. Lurquin C, De Smet C, Brasseur F et al. Two members of the human MAGEB gene family located in Xp.21.3 are expressed in tumors of various histological origins. *Genomics* 1997: 46: 397–408.
3. Lucas S, De Smet C, Arden K C et al. Identification of a new MAGE gene with tumor-specific expression by representational difference analysis. *Cancer Res* 1998: 58: 743–52.
4. Chomez P, De Backer O, Bertrand M, De Plaen E, Boon T, Lucas S. An overview of the MAGE gene family with the identification of all human members of the family. *Cancer Res* 2001: 61: 5544–51.
5. Haas G G, Jr., D'Cruz O J, De Bault L E. Distribution of human leukocyte antigen-ABC and -D/DR antigens in the unfixed human testis. *Am J Reprod Immunol Microbiol* 1988: 18: 47–51.
6. Hunt D F, Henderson R A, Shabanowitz J et al. Characterization of peptides bound to the class I MHC molecule HLA-A2.1 by mass spectrometry. *Science* 1992: 255: 1261–3.
7. Marchand M, Brichard V, van Baren N, Coulie P G. Biological and clinical developments in melanoma vaccines. *Exp Opin Biol Ther* 2001: 1: 497–510.
8. Jäger E, Jager D, Knuth A. Clinical cancer vaccine trials. *Curr Opin Immunol* 2002: 14: 178–82.
9. Marchand M, van Baren N, Weynants P et al. Tumor regressions observed in patients with metastatic melanoma treated with an antigenic peptide encoded by gene MAGE-3 and presented by HLA-A1. *Int J Cancer* 1999: 80: 219–30.
10. Thumer B, Haendle I, Roder C et al. Vaccination with MAGE-3A1 peptide-pulsed mature, monocyte-derived dendritic cells expands specific cytotoxic T cells and induces regression of some metastases in advanced stage IV melanoma. *J Exp Med* 1999: 190: 1669–78.
11. De Plaen E, Naerhuyzen B, De Smet C, Szikora J-P, Boon T. Alternative promoters of gene MAGE4a. *Genomics* 1997: 40: 305–13.
12. Duffour M-T, Chaux P, Lurquin C, Cornelis G, Boon T, van der Bruggen P. A MAGE-A4 peptide presented by HLA-A2 is recognized by cytolytic T lymphocytes. *Eur J Immunol* 1999: 29: 3329–37.
13. Traversari C, van der Bruggen P, Van den Eynde B et al. Transfection and expression of a gene coding for a human melanoma antigen recognized by autologous cytolytic T lymphocytes. *Immunogenetics* 1992: 35: 145–52.
14. Van Snick J, Vink A, Cayphas S, Uyttenhove C. Interleukin-HP1, a T cell-derived hybridoma growth factor that supports the in vitro growth of murine plasmocytomas. *J Exp Med* 1987: 165: 641–9.
15. Mavilio F, Ferrari G, Rossini S et al. Peripheral blood lymphocytes as target cells of retroviral vector-mediated gene transfer. *Blood* 1994: 83: 1988–97.
16. Espevik T, Nissen-Meyer J. A highly sensitive cell line, WEHI 164 clone 13, for measuring cytotoxic factor/tumor necrosis factor from human monocytes. *J Immunol Methods* 1986: 95: 99–105.
17. Hansen M B, Nielsen S E, Berg K. Re-examination and further development of a precise and rapid dye method for measuring cell growth/cell kill. *J Immunol Methods* 1989: 119: 203–10.
18. Chaux P, Luiten R, Demotte N et al. Identification of five MAGE-A1 epitopes recognized by cytolytic T lymphocytes obtained by in vitro stimulation with dendritic cells transduced with MAGE-A1. *J Immunol* 1999:163: 2928–36.
19. Rammensee H-G, Bachmann J, Stevanovic S. *MHC Ligands and Peptide Motifs*. New York: Springer, 1997.
20. Falk K, Rötzschke O, Grahovac B et al. Peptide motifs of HLA-B35 and -B37 molecules. *Immunogenetics* 1993: 38: 161–2.
21. Schultz E S, Zhang Y, Knowles R et al. A MAGE-3 peptide recognized on HLA-B35 and HLA-A1 by cytolytic T lymphocytes. *Tissue Antigens* 2001: 57: 103–9.
22. Luiten R, van der Bruggen P. A MAGE-A1 peptide is recognized on HLA-B7 human tumors by cytolytic T lymphocytes. *Tissue Antigens* 2000: 55: 149–52.
23. Traversari C, van der Bruggen P, Luescher I F et al. A nonapeptide encoded by human gene MAGE-1 is recognized on HLA-A1 by cytolytic T lymphocytes directed against tumor antigen MZ2-E. *J Exp Med* 1992: 176: 1453–7.
24. van der Bruggen P, Szikora J-P, Boël P et al. Autologous cytolytic T lymphocytes recognize a MAGE-1 nonapeptide on melanomas expressing HLA-Cw*1601. *Eur J Immunol* 1994: 24: 2134–40.
25. van der Bruggen P, Zhang Y, Chaux P et al. Tumor-specific shared antigenic peptides recognized by human T cells. *Immunol Rev* 2002: in press:
26. Chen C H, Huang G T, Lee H S et al. High frequency of expression of MAGE genes in human hepatocellular carcinoma. *Liver* 1999: 19: 110–4.
27. Dalerba P, Frascella E, Macino B et al. MAGE, BAGE and GAGE gene expression in human rhabdomyosarcomas. *Int J Cancer* 2001: 93: 85–90.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. An isolated peptide consisting of a fragment of SEQ ID NO:2 that comprises the amino acid sequence of SEQ ID No:5; wherein the peptide activates a CD8+ T-cell specific for MAGE-A4 when presented by an HLA Class-I molecule; wherein the isolated peptide consists of up to 10 amino acids of SEQ ID NO:2 consecutive to the N-terminus and/or the C-terminus of SEQ ID NO:5.

2. The isolated peptide of claim 1, wherein the isolated-peptide consists of an amino acid sequence set forth as SEQ ID NO:4, or SEQ ID NO:5.

3. A composition comprising the isolated peptide of claim 1 and an isolated HLA class I- or class II-binding peptide of a non-MAGE-A4 tumor antigen.

4. A composition comprising the isolated peptide of claim 2 and an isolated HLA class I- or class II-binding peptide of a non-MAGE-A4 tumor antigen.

5. A composition comprising the isolated peptide of claim 1 and a carrier.

6. The composition of claim 5, further comprising en adjuvant.

7. An isolated peptide consisting of a fragment of SEQ ID NO:2 that comprises the amino acid sequence set forth as SEQ ID NO:6, wherein the isolated peptide includes up to 10 amino acids of SEQ ID NO:2 consecutive to the N-terminus of SEQ ID NO:6.

8. A composition comprising the isolated peptide of claim 7 and an isolated HLA class I- or class II-binding peptide of a non-MAQE-A4 tumor antigen.

9. A composition comprising the isolated peptide of claim 7 and a carrier.

10. The composition of claim 9, further comprising an adjuvant.

11. The isolated peptide of claim 7, wherein the isolated-peptide consists of an amino acid sequences set forth as SEQ ID NO:3 or SEQ ID NO:6.

* * * * *

UNITED STATES PATENT AND TRADEMARK OFFICE
CERTIFICATE OF CORRECTION

PATENT NO. : 7,311,914 B2
APPLICATION NO. : 10/218095
DATED : December 25, 2007
INVENTOR(S) : Yi Zhang et al.

Page 1 of 1

It is certified that error appears in the above-identified patent and that said Letters Patent is hereby corrected as shown below:

Title page, item (73) Assignees should read as follows:

Ludwig Institute for Cancer Research, New York, NY (US); Fondazione Centro San Raffaele Del Monte Tabor, Milano (IT)

Signed and Sealed this
Tenth Day of July, 2012

David J. Kappos
*Director of the United States Patent and Trademark Office*

SEQUENCE LISTING

```
<160> NUMBER OF SEQ ID NOS: 63

<210> SEQ ID NO 1
<211> LENGTH: 954
<212> TYPE: DNA
<213> ORGANISM: Homo sapiens
```

<400> SEQUENCE: 1

| | | | | | |
|---|---|---|---|---|---|
| atgtcttctg | agcagaagag | tcagcactgc | aagcctgagg | aaggcgttga | ggcccaagaa | 60 |
| gaggccctgg | gcctggtggg | tgcacaggct | cctactactg | aggagcagga | ggctgctgtc | 120 |
| tcctcctcct | ctcctctggt | ccctggcacc | ctggaggaag | tgcctgctgc | tgagtcagca | 180 |
| ggtcctcccc | agagtcctca | gggagcctct | gccttaccca | ctaccatcag | cttcacttgc | 240 |
| tggaggcaac | ccaatgaggg | ttccagcagc | caagaagagg | aggggccaag | cacctcgcct | 300 |
| gacgcagagt | ccttgttccg | agaagcactc | agtaacaagg | tggatgagtt | ggctcatttt | 360 |
| ctgctccgca | agtatcgagc | caaggagctg | gtcacaaagg | cagaaatgct | ggagagagtc | 420 |
| atcaaaaatt | acaagcgctg | ctttcctgtg | atcttcggca | agcctccga | gtccctgaag | 480 |
| atgatctttg | gcattgacgt | gaaggaagtg | gaccccgcca | gcaacaccta | cacccttgtc | 540 |
| acctgcctgg | gcctttccta | tgatggcctg | ctgggtaata | atcagatctt | tcccaagaca | 600 |
| ggccttctga | taatcgtcct | gggcacaatt | gcaatggagg | gcgacagcgc | tctgaggag | 660 |
| gaaatctggg | aggagctggg | tgtgatgggg | gtgtatgatg | ggagggagca | cactgtctat | 720 |
| ggggagccca | ggaaactgct | cacccaagat | tgggtgcagg | aaaactacct | ggagtaccgg | 780 |
| caggtacccg | gcagtaatcc | tgcgcgctat | gagttcctgt | ggggtccaag | ggctctggct | 840 |
| gaaaccagct | atgtgaaagt | cctggagcat | gtggtcaggg | tcaatgcaag | agttcgcatt | 900 |
| gcctacccat | ccctgcgtga | agcagctttg | ttagaggagg | aagagggagt | ctga | 954 |

<210> SEQ ID NO 2
<211> LENGTH: 317
<212> TYPE: PRT
<213> ORGANISM: Homo sapiens

<400> SEQUENCE: 2

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Gln Glu Ala Ala Val Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
        115                 120                 125

Glu Leu Val Thr Lys Ala Glu Met Leu Glu Arg Val Ile Lys Asn Tyr
    130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
            180                 185                 190

Asn Asn Gln Ile Phe Pro Lys Thr Gly Leu Leu Ile Ile Val Leu Gly

-continued

```
                195                 200                 205
Thr Ile Ala Met Glu Gly Asp Ser Ala Ser Glu Glu Ile Trp Glu
        210                 215                 220
Glu Leu Gly Val Met Gly Val Tyr Asp Gly Arg Glu His Thr Val Tyr
225                 230                 235                 240
Gly Glu Pro Arg Lys Leu Leu Thr Gln Asp Trp Val Gln Asn Tyr
            245                 250                 255
Leu Glu Tyr Arg Gln Val Pro Gly Ser Asn Pro Ala Arg Tyr Glu Phe
            260                 265                 270
Leu Trp Gly Pro Arg Ala Leu Ala Glu Thr Ser Tyr Val Lys Val Leu
        275                 280                 285
Glu His Val Val Arg Val Asn Ala Arg Val Arg Ile Ala Tyr Pro Ser
        290                 295                 300
Leu Arg Glu Ala Ala Leu Leu Glu Glu Glu Gly Val
305                 310                 315
```

<210> SEQ ID NO 3
<211> LENGTH: 16
<212> TYPE: PRT
<213> ORGANISM: Homo sapiens

<400> SEQUENCE: 3

```
Phe Pro Val Ile Phe Gly Lys Ala Ser Glu Ser Leu Lys Met Ile Phe
1               5                   10                  15
```

<210> SEQ ID NO 4
<211> LENGTH: 16
<212> TYPE: PRT
<213> ORGANISM: Homo sapiens

<400> SEQUENCE: 4

```
Ser Glu Ser Leu Lys Met Ile Phe Gly Ile Asp Val Lys Glu Val Asp
1               5                   10                  15
```

<210> SEQ ID NO 5
<211> LENGTH: 10
<212> TYPE: PRT
<213> ORGANISM: Homo sapiens

<400> SEQUENCE: 5

```
Ser Glu Ser Leu Lys Met Ile Phe Gly Ile
1               5                   10
```

<210> SEQ ID NO 6
<211> LENGTH: 8
<212> TYPE: PRT
<213> ORGANISM: Homo sapiens

<400> SEQUENCE: 6

```
Ser Glu Ser Leu Lys Met Ile Phe
1               5
```

<210> SEQ ID NO 7
<211> LENGTH: 9
<212> TYPE: PRT
<213> ORGANISM: Homo sapiens

<400> SEQUENCE: 7

```
Ser Glu Ser Leu Lys Met Ile Phe Gly
1               5
```

```
<210> SEQ ID NO 8
<211> LENGTH: 9
<212> TYPE: PRT
<213> ORGANISM: Homo sapiens

<400> SEQUENCE: 8

Ser Glu Ser Leu Lys Met Ile Phe Ile
1               5

<210> SEQ ID NO 9
<211> LENGTH: 9
<212> TYPE: PRT
<213> ORGANISM: Homo sapiens

<400> SEQUENCE: 9

Ser Glu Ser Leu Lys Met Ile Phe Leu
1               5

<210> SEQ ID NO 10
<211> LENGTH: 10
<212> TYPE: PRT
<213> ORGANISM: Homo sapiens

<400> SEQUENCE: 10

Gly Val Tyr Asp Gly Arg Glu His Thr Val
1               5                   10

<210> SEQ ID NO 11
<211> LENGTH: 9
<212> TYPE: PRT
<213> ORGANISM: Homo sapiens

<400> SEQUENCE: 11

Glu Ala Asp Pro Thr Gly His Ser Tyr
1               5

<210> SEQ ID NO 12
<211> LENGTH: 9
<212> TYPE: PRT
<213> ORGANISM: Homo sapiens

<400> SEQUENCE: 12

Ser Ala Tyr Gly Glu Pro Arg Lys Leu
1               5

<210> SEQ ID NO 13
<211> LENGTH: 9
<212> TYPE: PRT
<213> ORGANISM: Homo sapiens

<400> SEQUENCE: 13

Glu Val Asp Pro Ile Gly His Leu Tyr
1               5

<210> SEQ ID NO 14
<211> LENGTH: 9
<212> TYPE: PRT
<213> ORGANISM: Homo sapiens

<400> SEQUENCE: 14

Phe Leu Trp Gly Pro Arg Ala Leu Val
1               5

<210> SEQ ID NO 15
<211> LENGTH: 10
```

```
<212> TYPE: PRT
<213> ORGANISM: Homo sapiens

<400> SEQUENCE: 15

Met Glu Val Asp Pro Ile Gly His Leu Tyr
1               5                   10

<210> SEQ ID NO 16
<211> LENGTH: 9
<212> TYPE: PRT
<213> ORGANISM: Homo sapiens

<400> SEQUENCE: 16

Ala Ala Arg Ala Val Phe Leu Ala Leu
1               5

<210> SEQ ID NO 17
<211> LENGTH: 8
<212> TYPE: PRT
<213> ORGANISM: Homo sapiens

<400> SEQUENCE: 17

Tyr Arg Pro Arg Pro Arg Arg Tyr
1               5

<210> SEQ ID NO 18
<211> LENGTH: 10
<212> TYPE: PRT
<213> ORGANISM: Homo sapiens

<400> SEQUENCE: 18

Ser Pro Ser Ser Asn Arg Ile Arg Asn Thr
1               5                   10

<210> SEQ ID NO 19
<211> LENGTH: 9
<212> TYPE: PRT
<213> ORGANISM: Homo sapiens

<400> SEQUENCE: 19

Val Leu Pro Asp Val Phe Ile Arg Cys
1               5

<210> SEQ ID NO 20
<211> LENGTH: 10
<212> TYPE: PRT
<213> ORGANISM: Homo sapiens

<400> SEQUENCE: 20

Val Leu Pro Asp Val Phe Ile Arg Cys Val
1               5                   10

<210> SEQ ID NO 21
<211> LENGTH: 9
<212> TYPE: PRT
<213> ORGANISM: Homo sapiens

<400> SEQUENCE: 21

Glu Glu Lys Leu Ile Val Val Leu Phe
1               5

<210> SEQ ID NO 22
<211> LENGTH: 9
<212> TYPE: PRT
```

```
<213> ORGANISM: Homo sapiens

<400> SEQUENCE: 22

Glu Glu Lys Leu Ser Val Val Leu Phe
1               5

<210> SEQ ID NO 23
<211> LENGTH: 10
<212> TYPE: PRT
<213> ORGANISM: Homo sapiens

<400> SEQUENCE: 23

Ala Cys Asp Pro His Ser Gly His Phe Val
1               5                   10

<210> SEQ ID NO 24
<211> LENGTH: 10
<212> TYPE: PRT
<213> ORGANISM: Homo sapiens

<400> SEQUENCE: 24

Ala Arg Asp Pro His Ser Gly His Phe Val
    1               5                   10

<210> SEQ ID NO 25
<211> LENGTH: 9
<212> TYPE: PRT
<213> ORGANISM: Homo sapiens

<400> SEQUENCE: 25

Ser Tyr Leu Asp Ser Gly Ile His Phe
1               5

<210> SEQ ID NO 26
<211> LENGTH: 9
<212> TYPE: PRT
<213> ORGANISM: Homo sapiens

<400> SEQUENCE: 26

Ser Tyr Leu Asp Ser Gly Ile His Ser
1               5

<210> SEQ ID NO 27
<211> LENGTH: 9
<212> TYPE: PRT
<213> ORGANISM: Homo sapiens

<400> SEQUENCE: 27

Met Leu Leu Ala Val Leu Tyr Cys Leu
1               5

<210> SEQ ID NO 28
<211> LENGTH: 9
<212> TYPE: PRT
<213> ORGANISM: Homo sapiens

<400> SEQUENCE: 28

Tyr Met Asn Gly Thr Met Ser Gln Val
1               5

<210> SEQ ID NO 29
<211> LENGTH: 9
<212> TYPE: PRT
<213> ORGANISM: Homo sapiens
```

<400> SEQUENCE: 29

Ala Phe Leu Pro Trp His Arg Leu Phe
1               5

<210> SEQ ID NO 30
<211> LENGTH: 9
<212> TYPE: PRT
<213> ORGANISM: Homo sapiens

<400> SEQUENCE: 30

Ser Glu Ile Trp Arg Asp Ile Asp Phe
1               5

<210> SEQ ID NO 31
<211> LENGTH: 9
<212> TYPE: PRT
<213> ORGANISM: Homo sapiens

<400> SEQUENCE: 31

Tyr Glu Ile Trp Arg Asp Ile Asp Phe
1               5

<210> SEQ ID NO 32
<211> LENGTH: 15
<212> TYPE: PRT
<213> ORGANISM: Homo sapiens

<400> SEQUENCE: 32

Gln Asn Ile Leu Leu Ser Asn Ala Pro Leu Gly Pro Gln Phe Pro
1               5                   10                  15

<210> SEQ ID NO 33
<211> LENGTH: 15
<212> TYPE: PRT
<213> ORGANISM: Homo sapiens

<400> SEQUENCE: 33

Asp Tyr Ser Tyr Leu Gln Asp Ser Asp Pro Asp Ser Phe Gln Asp
1               5                   10                  15

<210> SEQ ID NO 34
<211> LENGTH: 10
<212> TYPE: PRT
<213> ORGANISM: Homo sapiens

<400> SEQUENCE: 34

Glu Ala Ala Gly Ile Gly Ile Leu Thr Val
1               5                   10

<210> SEQ ID NO 35
<211> LENGTH: 9
<212> TYPE: PRT
<213> ORGANISM: Homo sapiens

<400> SEQUENCE: 35

Ala Ala Gly Ile Gly Ile Leu Thr Val
1               5

<210> SEQ ID NO 36
<211> LENGTH: 9
<212> TYPE: PRT
<213> ORGANISM: Homo sapiens

<400> SEQUENCE: 36

-continued

Ile Leu Thr Val Ile Leu Gly Val Leu
1               5

<210> SEQ ID NO 37
<211> LENGTH: 9
<212> TYPE: PRT
<213> ORGANISM: Homo sapiens

<400> SEQUENCE: 37

Lys Thr Trp Gly Gln Tyr Trp Gln Val
1               5

<210> SEQ ID NO 38
<211> LENGTH: 9
<212> TYPE: PRT
<213> ORGANISM: Homo sapiens

<400> SEQUENCE: 38

Ile Thr Asp Gln Val Pro Phe Ser Val
1               5

<210> SEQ ID NO 39
<211> LENGTH: 9
<212> TYPE: PRT
<213> ORGANISM: Homo sapiens

<400> SEQUENCE: 39

Tyr Leu Glu Pro Gly Pro Val Thr Ala
1               5

<210> SEQ ID NO 40
<211> LENGTH: 10
<212> TYPE: PRT
<213> ORGANISM: Homo sapiens

<400> SEQUENCE: 40

Leu Leu Asp Gly Thr Ala Thr Leu Arg Leu
1               5                   10

<210> SEQ ID NO 41
<211> LENGTH: 10
<212> TYPE: PRT
<213> ORGANISM: Homo sapiens

<400> SEQUENCE: 41

Val Leu Tyr Arg Tyr Gly Ser Phe Ser Val
1               5                   10

<210> SEQ ID NO 42
<211> LENGTH: 9
<212> TYPE: PRT
<213> ORGANISM: Homo sapiens

<400> SEQUENCE: 42

Leu Tyr Val Asp Ser Leu Phe Phe Leu
1               5

<210> SEQ ID NO 43
<211> LENGTH: 12
<212> TYPE: PRT
<213> ORGANISM: Homo sapiens

<400> SEQUENCE: 43

Lys Ile Ser Gly Gly Pro Arg Ile Ser Tyr Pro Leu
1               5                   10

<210> SEQ ID NO 44
<211> LENGTH: 9
<212> TYPE: PRT
<213> ORGANISM: Homo sapiens

<400> SEQUENCE: 44

Tyr Met Asp Gly Thr Met Ser Gln Val
1               5

<210> SEQ ID NO 45
<211> LENGTH: 11
<212> TYPE: PRT
<213> ORGANISM: Homo sapiens

<400> SEQUENCE: 45

Ser Leu Leu Met Trp Ile Thr Gln Cys Phe Leu
1               5                   10

<210> SEQ ID NO 46
<211> LENGTH: 9
<212> TYPE: PRT
<213> ORGANISM: Homo sapiens

<400> SEQUENCE: 46

Ser Leu Leu Met Trp Ile Thr Gln Cys
1               5

<210> SEQ ID NO 47
<211> LENGTH: 9
<212> TYPE: PRT
<213> ORGANISM: Homo sapiens

<400> SEQUENCE: 47

Gln Leu Ser Leu Leu Met Trp Ile Thr
1               5

<210> SEQ ID NO 48
<211> LENGTH: 8
<212> TYPE: PRT
<213> ORGANISM: Homo sapiens

<400> SEQUENCE: 48

Ser Glu Ser Leu Gln Leu Val Phe
1               5

<210> SEQ ID NO 49
<211> LENGTH: 10
<212> TYPE: PRT
<213> ORGANISM: Homo sapiens

<400> SEQUENCE: 49

Ser Glu Ser Leu Gln Leu Val Phe Gly Ile
1               5                   10

<210> SEQ ID NO 50
<211> LENGTH: 8
<212> TYPE: PRT
<213> ORGANISM: Homo sapiens

<400> SEQUENCE: 50

Ser Glu Tyr Leu Gln Leu Val Phe
1               5

```
<210> SEQ ID NO 51
<211> LENGTH: 10
<212> TYPE: PRT
<213> ORGANISM: Homo sapiens

<400> SEQUENCE: 51

Ser Glu Tyr Leu Gln Leu Val Phe Gly Ile
1               5                   10

<210> SEQ ID NO 52
<211> LENGTH: 8
<212> TYPE: PRT
<213> ORGANISM: Homo sapiens

<400> SEQUENCE: 52

Ser Ser Ser Leu Gln Leu Val Phe
1               5

<210> SEQ ID NO 53
<211> LENGTH: 10
<212> TYPE: PRT
<213> ORGANISM: Homo sapiens

<400> SEQUENCE: 53

Ser Ser Ser Leu Gln Leu Val Phe Gly Ile
1               5                   10

<210> SEQ ID NO 54
<211> LENGTH: 8
<212> TYPE: PRT
<213> ORGANISM: Homo sapiens

<400> SEQUENCE: 54

Ser Asp Ser Leu Gln Leu Val Phe
1               5

<210> SEQ ID NO 55
<211> LENGTH: 10
<212> TYPE: PRT
<213> ORGANISM: Homo sapiens

<400> SEQUENCE: 55

Ser Asp Ser Leu Gln Leu Val Phe Gly Ile
1               5                   10

<210> SEQ ID NO 56
<211> LENGTH: 8
<212> TYPE: PRT
<213> ORGANISM: Homo sapiens

<400> SEQUENCE: 56

Ser Glu Cys Met Gln Val Ile Phe
1               5

<210> SEQ ID NO 57
<211> LENGTH: 10
<212> TYPE: PRT
<213> ORGANISM: Homo sapiens

<400> SEQUENCE: 57

Ser Glu Cys Met Gln Val Ile Phe Gly Ile
1               5                   10

<210> SEQ ID NO 58
<211> LENGTH: 8
```

```
<212> TYPE: PRT
<213> ORGANISM: Homo sapiens

<400> SEQUENCE: 58

Ser Glu Cys Met Leu Leu Val Phe
1               5

<210> SEQ ID NO 59
<211> LENGTH: 10
<212> TYPE: PRT
<213> ORGANISM: Homo sapiens

<400> SEQUENCE: 59

Ser Glu Cys Met Leu Leu Val Phe Gly Ile
1               5                   10

<210> SEQ ID NO 60
<211> LENGTH: 8
<212> TYPE: PRT
<213> ORGANISM: Homo sapiens

<400> SEQUENCE: 60

Ser Val Cys Met Gln Leu Leu Phe
1               5

<210> SEQ ID NO 61
<211> LENGTH: 10
<212> TYPE: PRT
<213> ORGANISM: Homo sapiens

<400> SEQUENCE: 61

Ser Val Cys Met Gln Leu Leu Phe Gly Ile
1               5                   10

<210> SEQ ID NO 62
<211> LENGTH: 8
<212> TYPE: PRT
<213> ORGANISM: Homo sapiens

<400> SEQUENCE: 62

Ser Glu Tyr Leu Gln Leu Val Phe
1               5

<210> SEQ ID NO 63
<211> LENGTH: 10
<212> TYPE: PRT
<213> ORGANISM: Homo sapiens

<400> SEQUENCE: 63

Ser Glu Tyr Leu Gln Leu Val Phe Gly Ile
1               5                   10
```